(12) United States Patent
Okayama et al.

(10) Patent No.: US 11,663,929 B2
(45) Date of Patent: May 30, 2023

(54) HEART MODEL

(71) Applicants: OSAKA UNIVERSITY, Suita (JP); JMC CORPORATION, Yokohama (JP); FUYO CORPORATION, Nishitokyo (JP)

(72) Inventors: Keita Okayama, Suita (JP); Yasushi Sakata, Suita (JP); Shinsuke Nanto, Nishinomiya (JP); Daichi Watanabe, Yokohama (JP); Makoto Inada, Yokohama (JP); Munekuni Sato, Nishitokyo (JP)

(73) Assignees: OSAKA UNIVERSITY, Suita (JP); JMC CORPORATION, Yokohama (JP); FUYO CORPORATION, Nishitokyo (JP)

( * ) Notice: Subject to any disclaimer, the term of this patent is extended or adjusted under 35 U.S.C. 154(b) by 354 days.

(21) Appl. No.: 17/154,119

(22) Filed: Jan. 21, 2021

(65) Prior Publication Data

US 2021/0142695 A1    May 13, 2021

Related U.S. Application Data

(60) Division of application No. 15/718,682, filed on Sep. 28, 2017, now Pat. No. 10,937,337, which is a continuation of application No. PCT/JP2016/057000, filed on Mar. 7, 2016.

(30) Foreign Application Priority Data

Mar. 30, 2015  (JP) .................................. 2015-068186
Nov. 9, 2015  (JP) .................................. 2015-219184

(51) Int. Cl.
| | | |
|---|---|---|
| G09B 23/32 | (2006.01) | |
| G09B 23/30 | (2006.01) | |
| A61B 90/00 | (2016.01) | |
| G09B 23/28 | (2006.01) | |
| G09B 23/34 | (2006.01) | |

(52) U.S. Cl.
CPC ............ *G09B 23/303* (2013.01); *A61B 90/00* (2016.02); *G09B 23/286* (2013.01); *G09B 23/32* (2013.01); *G09B 23/34* (2013.01)

(58) Field of Classification Search
None
See application file for complete search history.

(56) References Cited

FOREIGN PATENT DOCUMENTS

JP        2013213986 A    * 10/2013

* cited by examiner

*Primary Examiner* — James B Hull
(74) *Attorney, Agent, or Firm* — Manabu Kanesaka

(57) ABSTRACT

A heart model is retained in a container for a catheter simulator. The container includes an accommodating unit for accommodating a liquid, having side walls and a bottom surface, a connection unit attached to one of the side walls and retaining the heart model, and an installation part provided on one of the side walls. The installation part is configured to insert a catheter from an outside of the container into the simulated blood vessel of the heart model. The connection unit includes a holding protrusion protruding inside the accommodating unit, and a communicating hole. A front end of the holding protrusion is open so that the heart model is detachable from and reattachable to the holding protrusion by inserting and extracting a terminal of the heart model.

15 Claims, 13 Drawing Sheets

HEART MODEL

CROSS-REFERENCE TO RELATED APPLICATION

This is a divisional application of Ser. No. 15/718,682 filed on Sep. 28, 2017, which is a continuation application of PCT/JP2016/57000 filed on Mar. 7, 2016, claiming a priority of Japanese Patent Applications No. 2015-68186 filed on Mar. 30, 2015 and No. 2015-219184 filed on Nov. 9, 2015, the disclosure of which is incorporated herein.

TECHNICAL FIELD

The present invention relates to a heart model.

BACKGROUND ART

In the medical settings, for the purpose of performing an examination or treatment of an organ such as heart, a method of inserting a catheter through a vein in the armor leg and causing the catheter to reach the organ, is conventionally used. In regard to this catheter procedure, various simulators have been suggested in order to promote acquisition or proficiency of the operating techniques, and in addition to the training that utilizes computerized simulators, in recent years, there have been proposed simulators by which training based on a tactile sensation that is closer to that of the actual catheter operation.

For example, Patent Document 1 discloses a training apparatus (simulator) which circulates simulated blood (liquid) using simulated organs and simulated blood vessels that have elasticity and the like to the same extent as those of live organs. This simulator reduces the labor needed for the preparation and aftermaths associated with the training, by circulating a liquid, and the simulator also enables training for a catheter operation based on X-ray imaging. Furthermore, by causing a heart model (simulated heart) to pulsate (periodical contractile motion), the simulator enables training for the catheter procedures concerning the coronary arteries in a pulsating state, and enables training in an environment closer to the reality.

The inventors of the present invention have suggested a catheter simulator that realizes a training closer to the reality with a more convenient configuration, in the patent application described above (Patent Document 2). The catheter simulator according to the above-mentioned patent application has a configuration in which the flow of unnatural simulated blood (liquid) occurring in the coronary arteries is suppressed, the number of component parts (an electronic valve, a pressure sensor, an electronic valve controller, and the like) required to make a heart model to pulsate is reduced as much as possible, and an X-ray imaging system is not essentially needed (training by visual inspection is also possible).

CITATION LIST

Patent Document

Patent Document 1: JP 2014-170075 A
Patent Document 2: PCT/JP2014/079683

SUMMARY OF THE INVENTION

Problem to be Solved by the Invention

Since the catheter simulator disclosed in Patent Document 1 described above has a structure in which a liquid (simulated blood) is supplied to a coronary artery through the aortic side, the catheter simulator is in a condition that is different from the blood flow of a real heart part. As a result, it becomes difficult to realize a blood flow in the coronary artery similar to that in the human body, and the blood flow rate thereof, and thus training cannot be carried out in the same circumstances as in the coronary artery catheterization and surgery that are actually carried out. Furthermore, since the catheter simulator has a structure in which a liquid is circulated in the main body of the heart by connecting a supply tube and a discharge tube to the main body of the heart, and the liquid is also supplied to the inside of the main body through the coronary artery, unnatural flow may occur inside the main body, or a flow going back to the coronary artery may occur. Accordingly, when a catheter is inserted into the coronary artery, it is necessary to cope with the unnatural flow that is not observed in a real human body.

In the prior art technologies, the supply amount of the liquid that flows into a heart model is periodically varied in order to cause the heart model to pulsate. In order to control this supply amount, component parts such as an electronic valve, a pressure sensor, and an electronic valve controller are used, and there is a problem that the structure of the simulator becomes complicated.

The problem of the prior art technologies described above can be solved by the invention suggested in the above-mentioned patent application (Patent Document 2); however, the catheter simulator previously suggested requires a pump that produces a pulsatile flow. Also, there is room for improvement as for a heart model installed inside the container because it is intended only for an enhancement of technologies concerning the coronary artery.

The catheter operation for the heart may also be carried out inside the heart in addition to the coronary arteries at the surface of the heart, and thus it is considered that it will be helpful for the enhancement of physicians' technique if the training for catheter procedures of such multiple patterns is made more convenient. Specifically, when heart models corresponding to various types of examination or surgery are prepared, and catheter procedures are trained by setting them in optimal conditions, the competence of the user can be effectively improved in accordance with various types of heart diseases.

The present invention was achieved as a result of paying attention to the circumstances described above, and an object of the present invention is to provide a container for a catheter simulator, the container enabling the training for various catheter operations to be conveniently carried out. It is another object of the present invention to provide a heart model that is installed in such a container for a catheter simulator and enables the simulation of various catheter procedures.

Means for Solving Problem

In order to achieve the objects described above, the present invention provides a container for a catheter simulator comprising: an accommodating unit for accommodating a liquid, the accommodating unit being defined by side walls and a bottom face; a connection unit that can retain any one of the heart models selected from a four-chamber heart model, a coronary artery model, and a TAVI model; the heart model is installed in the accommodating unit that is filled with a liquid; and an installation part for inserting a catheter from the outside of the container into simulated blood vessels of the heart model.

The container for a catheter simulator described above is provided with a connection unit for retaining a heart model. In each of the heart models described above, terminals connected to the connection units of the container are formed, and when the terminals are joined to the connection units of the container, the heart model is retained in a state of floating in the container filled with a liquid. The term "terminal" as used herein is a part that has been formed integrally with the main body of the heart in advance for an application intended for connection to the container, on the outside of the main body of the heart model, and this part is an element that does not exist in a real human heart.

When the terminals of the heart model are detached from the connection units of the container, simulation can be performed by switching various heart models (four-chamber heart model, coronary artery model, and TAVI (Transcatheter Aortic Valve Implantation) model, while using the same container.

For example, a coronary artery model is connected to the container so as to be installed in a state of floating in the liquid held in the container, and training for the catheter procedure for coronary arteriography is implemented. Subsequently, the coronary artery model is taken out from the container, and a TAVI model is connected to the container so as to be installed in a state of floating in the liquid. Then, simulation of the transcatheter aortic valve implantation can be continuously carried out in a state in which the container filled with a liquid is still used. As such, when the container for catheter simulation according to the present invention is used, training for various heart catheter operations can be continuously carried out conveniently, by switching various heart models in accordance with intended simulations.

The heart models described above are formed from materials having elasticity close to the human heart, and a trainee selects and uses any one of a four-chamber heart model, a coronary artery model, and a TAVI model according to the purpose of simulation. In the case of using the coronary artery model and the TAVI model, it is preferable that an external pump that produces a pulsatile flow is connected to the container, and the pulsatile flow is caused to flow into these heart models. Simulations using these heart models such as coronary arteriography and transcatheter aortic valve implantation are generally affected greatly by pulses at the time of catheter operation. Therefore, it is desirable to simulate a pulse similar to that of human heart in the coronary artery model and the TAVI model, and to provide a condition closer to the reality to the trainee.

Meanwhile, in the case of using the four-chamber heart model, the external pump may not be connected to the container. It is because examinations or surgeries that involve simulations using the four-chamber heart model are primarily ablation concerning arrhythmia, myocardiac biopsy, and right heart catheterization, and generally, it is not much necessary to consider the influence of pulses at the time of catheter operation. That is, when the container for catheter simulation according to the present invention and the four-chamber heart model are used, simulation using the four-chamber heart model can be carried out even in a state in which the external pump is not connected to the container. In this case, training can be carried out without being restricted by the pump or the supply of electric power needed for the operation of the pump.

However, depending on the selection of the trainee, it is also possible to perform simulation in a state in which the pump is connected to the container even in a situation in which the four-chamber heart model is used. For example, as described above, in a case in which the four-chamber heart model is used for simulation successively after the use of the coronary artery model, simulation can be directly continued without detaching the pump at the time of switching these heart models. That is, the use of the pump can be freely selected by a trainee depending on the type, details, procedure, and the like of the simulation. As such, the container for catheter simulation according to the present invention is configured such that various heart models can be switched, and also, if necessary, whether a pump will be used can also be selected.

The container for catheter simulation described above is provided with a heart model (a four-chamber heart model, a coronary artery model, or a TAVI model) produced exclusively for the container.

The four-chamber heart model, which is one of the heart models according to the present invention, has a main body of heart; venae cavae (superior vena cava and inferior vena cava) that are connected to the main body of heart; and a terminal (support unit) that can be connected to the connection unit of the container, and these parts are integrally formed. In the inside of the main body of heart, a right atrium, a right ventricle, a left atrium, and a left ventricle are formed, similarly to the human heart. This four-chamber heart model may not include a coronary artery that exists in the human heart, at the surface of the main body of heart.

When the four-chamber heart model is used, catheter procedures concerning the interior of the heart, for example, catheter simulations related to a electrophysiologic test such as mapping for detecting electrically abnormal sites inside the heart, ablation therapy for cauterizing the abnormal sites, myocardiac biopsy of collecting the tissue of a site suspected to have a disease for the purpose of a pathological examination, and right heart catheterization for measuring the pressure inside the heart or the cardiac output, can be carried out.

The coronary artery model, which is one of the heart models according to the present invention, has a main body of heart; coronary arteries at the surface of the main body of heart; an aorta connected to the superior side of the main body of heart; and a terminal (inflow tube) provided at the apex of the main body of heart (caudal side of the main body of heart), and these parts are formed integrally. The end of the inflow tube is open and is connected to the connection unit of the container, and also, the inflow tube serves as a pathway through which a pulsatile flow sent out by the above-mentioned pump flows into the main body of heart. The interior of the main body of heart is a cavity, and coronary arteries are formed on the surface of the main body of heart in the same manner as in the case of the human heart. The pulsatile flow supplied from the pump flows into the main body of heart through the inflow tube and passes through the inside of the main body of heart, which is a cavity, and a portion of the pulsatile flow flows into the coronary arteries, while the remaining portion reaches the aorta.

When the pulsatile flow flows into the interior of the main body of heart and the coronary arteries, and a liquid is supplied by heartbeats similar to those of the human heart, catheter procedures concerning pulsating coronary arteries, for example, simulations concerning coronary arteriography and coronary angioplasty can be carried out.

The TAVI model has a main body of heart; an aorta connected to the superior side of the main body of heart; and a terminal (inflow tube) provided at the apex of the main body of heart (caudal side of the main body of heart), and these parts are formed integrally. In the inside of the main body of heart, aright atrium, a right ventricle, a left atrium, a left ventricle, and the like are formed similarly to the human heart. Similarly to the coronary artery model, the end of the inflow tube is open and is connected to the connection unit of the container, and the inflow tube serves as a pathway through which a pulsatile flow sent out by the above-mentioned pump flows into the main body of heart. In the inside the main body of heart, the pulsatile flow flows in, and a liquid is supplied by heartbeats similar to those of the human heart. Thus, when a pulsatile flow is supplied from the pump to the TAVI model, catheter therapy for the interior of a pulsating heart (transcatheter aortic valve implantation or the like) can be carried out.

It is also acceptable for the TAVI model that the right atrium, right ventricle, left atrium, and left ventricle are not formed, and the interior of the main body of heart is a cavity. When an aorta connected to the superior side of the main body of heart protrudes into the interior of the main body of heart similar to that in the human body, and an aortic valve is formed at the end of the aorta, transcatheter aortic valve implantation directed to the simulation of the TAVI model can be carried out.

Effect of the Invention

When the container for a catheter simulator of the present invention and various heart models installed in the container are used, catheter procedures of a plurality of patterns in accordance with different modes of examination or surgery can be carried out more conveniently.

BRIEF DESCRIPTION OF DRAWINGS

FIG. 7A is a general view of a state in which an aortic valve is mounted, while FIG. 7B is a partial view of the opening of the aorta and the aortic valve in a state in which the aortic valve has been detached;

MODE(S) FOR CARRYING OUT THE INVENTION

Hereinafter, embodiments of the present invention will be explained with reference to the drawings.

Figure 1:
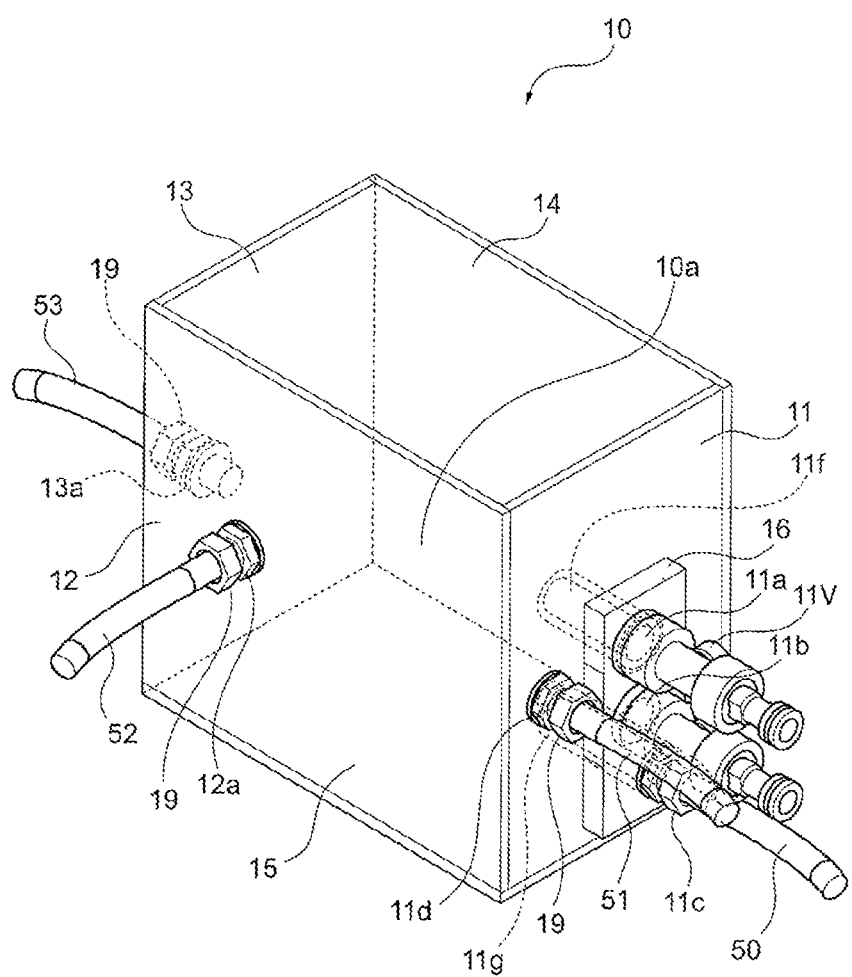
FIG. 1 is a diagram illustrating an embodiment of a container for a catheter simulator according to the present invention.

FIG. 1 is a diagram illustrating an embodiment of the container for a catheter simulator according to the present invention. First, the container for a catheter simulator will be explained with reference to FIG. 1.

The container 10 for a catheter simulator of the present embodiment is configured as a container in which an accommodating unit 10a for accommodating a liquid (not shown in the diagram) such as water or electrolyzed water is defined by side walls 11 to 14 of four faces and a bottom face 15. On the side walls, connection units 11a and 11c capable of retaining a heart model connected thereto (the four-chamber heart model of FIG. 3 (right heart model 20 according to the present embodiment), the coronary artery model 30 of FIG. 4, the TAVI model 40 of FIG. 5, the TAVI model 80 of FIG. 6, or the TAVI model 100 of FIG. 12) while having the accommodating unit 10a filled with a liquid; catheter installation parts 11d, 12a, and 13a for inserting catheters from the outside of the container 10 to the simulated blood vessels formed integrally with the heart model; and a discharge port 11b for discharging the liquid in the accommodating unit 10a to a pulsatile flow producing pump 60 (see FIG. 12; hereinafter, referred to as pump), are formed, and for example, these parts are installed in the positional relation illustrated in FIG. 1. The connection units 11a and 11c also play the role of installation parts for inserting catheters from the outside of the container 10.

The side walls 11 to 14 and the bottom face 15 are produced from a material having a strength that enables stable accommodation of a liquid and a heart model, and the shape of the side walls 11 to 14 and the bottom face 15 may be any shape capable of stably accommodating the liquid and the heart model, such as a rectangular shape, a rounded shape, or a shape combining those shapes. It is also preferable that the material for the side walls 11 to 14 and the bottom face 15 has is transparent. When the side walls and the bottom face are transparent, it is made possible to observe the behavior of the heart model installed inside the container 10 or the catheters to be inserted from the outside of the container 10 by visual inspection during a simulation. Examples of a material having such strength and transparency include an acrylic resin, polycarbonate, PET, and polystyrene.

Even in a case in which the container 10 is produced from a material that a trainee can visually recognize, when a camera is installed, and the image is displayed by a monitor or the like, or when X-ray radioscopy is performed, and the image is displayed by a monitor or the like, a simulation of comprehending the behavior of the catheters only through the monitor can be achieved, and it is also possible to realize a condition closer to the reality. Visual recognition, checking of monitor display, or use of X-ray imaging can be selected in accordance with the stage or details of the training.

The upper side of the container 10 is opened, and an openable lid may be provided here. Thereby, when preparation or aftermaths for training, such as an operation of filling the accommodating unit 10a with a liquid, and an operation installing a heart model in the liquid, are carried out, the operations can be efficiently achieved through the opening at the top face of the container.

In the present embodiment, the connection units 11a and 11c are configured to be approximately cylindrical in shape, and the connection units penetrate through the side wall 11, and respectively protrude toward the outside of the container 10. In this case, it is preferable that holding protrusions 11f and 11g that protrude toward the container accommodating unit 10a side are formed at the connection units 11a and 11c, and thereby, a heart model can be easily connected (retained) by plugging in the terminals of the heart model. Meanwhile, at the connection unit 11a of the present embodiment, a supply tube 63 of the pump 60 described above (see FIG. 12) is connected to the end protruding to the outside of the container 10. Therefore, at the connection unit 11a and the holding protrusion 11f, a communicating hole for passing the liquid sent from the pump 60 is formed, and in a case in which the pump 60 is operated, the communicating hole also accomplishes the role as a liquid inlet port from the pump 60. Since the connection unit 11c has a function as an installation part for a catheter, continuous holes through which catheters are inserted are formed at the connection unit 11c and the holding protrusion 11g.

The connection unit 11a and the discharge port 11b both have a valve 11V for opening and closing (only the connection unit 11a side is shown). This valve 11V for opening and closing is closed when the pump 60 is detached from the container 10 after completion of a simulation, and thereby the liquid in the accommodating unit 10a is prevented from escaping to the outside of the container 10.

The connection unit 11c is connected to an inlet tube 50 through which a catheter that is operated by a trainee is inserted from the outside of the container 10. Furthermore, the side wall 11 is provided with an installation part 11d to which a catheter inlet tube 51 is connected. The connection unit 11c and the installation part 11d are configured to be approximately cylindrical in shape, and the connection unit and the installation part penetrate through the side wall 11 and protrude to the outside of the container 10. The connection unit 11c and the installation part 11d have a connection mechanism that can be operated from the outside of the container 10. The connection mechanism has, for example, a structure that can fix or release the inlet tubes 50 and 51 when operating members (nuts) 19 are rotated by inserting the inlet tubes, and thus, the operation of attaching and detaching the inlet tubes can be carried out easily. The inlet tubes 50 and 51 may also have the tube ends penetrated into the accommodating unit 10a when the inlet tubes are connected to the connection unit and the installation part. Furthermore, it is not necessarily essential for the connection units 11a and 11c and the installation part 11d to be disposed on the same side wall.

On the side wall 11, an auxiliary plate 16 that increases the strength of the side wall 11 may be adhered. When strength reinforcement is attempted by means of the auxiliary plate 16, the overall weight of the container 10 can be reduced, as compared to the case in which strength is increased by making the entirety of the side wall 11 thicker. In a case in which visibility for the catheter that passes through is deteriorated by bonding the auxiliary plate 16 to the side wall 11, only at the surface where increase of strength is needed in the side wall 11, the thickness of the side wall may be increased. It is preferable that the side wall is produced into a flat plate shape without surface unevenness in order to enhance the visibility by eliminating refraction of light.

According to the present embodiment, the side wall 12 is provided with an installation part 12a that is connected to an inlet tube 52 through which a catheter operated by a trainee is introduced from the outside of the container 10, and similarly, the side wall 13 is provided with an installation part 13a that is connected to a catheter inlet tube 53. These installation parts 12a and 13a may be disposed on the same side wall.

During an actual simulation, the accommodating unit of the container 10a is filled with a liquid such as water, and a heart model is installed in the liquid in a floating state. Since the heart model is in a floating state, the trainee may have a feeling of touch that is closer to the reality at the time of catheter operation. That is, a heart model can be installed in a liquid in a floating state, by connecting (retaining) the heart model to the connection units 11a and 11c provided on the side walls of the container. It is also acceptable that, for example, a holder for exclusive use is installed at the bottom face of the container, and the heart model is retained in the liquid such that the heart model is supported from below, without providing a connection unit on the side wall.

Since the elements accommodated in the container 10 include only a heart model having the same size as that of the human heart, and a liquid for floating the heart model, the container 10 can be miniaturized. The external dimension of the container 10 according to the present embodiment is about 20 cm×20 cm×15 cm, and the amount of the liquid (water) needed to be filled in the container is merely approximately 3 L to 6 L. When the container 10 is miniaturized, waste of the space of the site of performing simulations can be eliminated, and the storage characteristics and transportability of the container 10 and so the catheter simulator that uses the container 10 can be enhanced. Furthermore, since the amount of water filled in the accommodating unit 10a of the container is only 6 L or less, even at a place where tap water cannot be utilized, simulation can be carried out by transporting water using a tank or the like. Thus, the range of selection for the place of performing simulation becomes wider. Furthermore, the weight of the container filled with water is light to the extent that the trainee can handle the container by himself or herself, setting up or cleaning up of simulations can also be carried out without the restriction on assistants.

As will be described below, a trainee selects the installation part (connection unit) through which a catheter is introduced, from among the inlet tubes 50 to 53, depending on the heart model used or the details of the simulation. The inlet tubes 50 to 53 each have a catheter installation terminal at the tube end on the external side of the container 10, and the installation terminal has a function of preventing the liquid filling the inlet tubes 50 to 53 from leaking to the outside (valve function), and also has a structure in which a trainee can introduce a catheter through the inlet tubes 50 to 53 and withdraw the catheter therefrom. According to the present embodiment, the inlet tube 50 is connected, through the installation part 11c, to the aorta 32, 45, 82, or 102 formed in the coronary artery model 30 (FIG. 4), the TAVI model 40 (FIG. 5), 80 (FIG. 6) or 100 (FIG. 7A), respectively. Similarly, the inlet tube 51 is connected to the inferior vena cava 22 formed in the right heart model 20 (FIG. 3) through the installation part 11d; the inlet tube 52 is connected to the right subclavian artery 34 or 46 formed in the coronary artery model 30 or the TAVI model 40, respectively, through the installation part 12a; and the inlet tube 53 is connected to the superior vena cava 23 or 43 formed in the right heart model 20 or the TAVI model 40, respectively, through the installation part 13a.

Next, an embodiment in which a right heart model 20 (one embodiment of the four-chamber heart model), which is one of the heart models according to the present invention, is installed in the accommodating unit 10a of the container 10 will be explained with reference to FIG. 2 and FIG. 3.

When a catheter is caused to reach the interior of the heart, it is general to insert the catheter through the right ventricle system (right atrium and right ventricle) that is connected to a large blood vessel directed to the heart (vena cava), therefore the right heart model 20 is formed for the simulation of catheterization, surgery or the like inside the heart.

Figure 3:
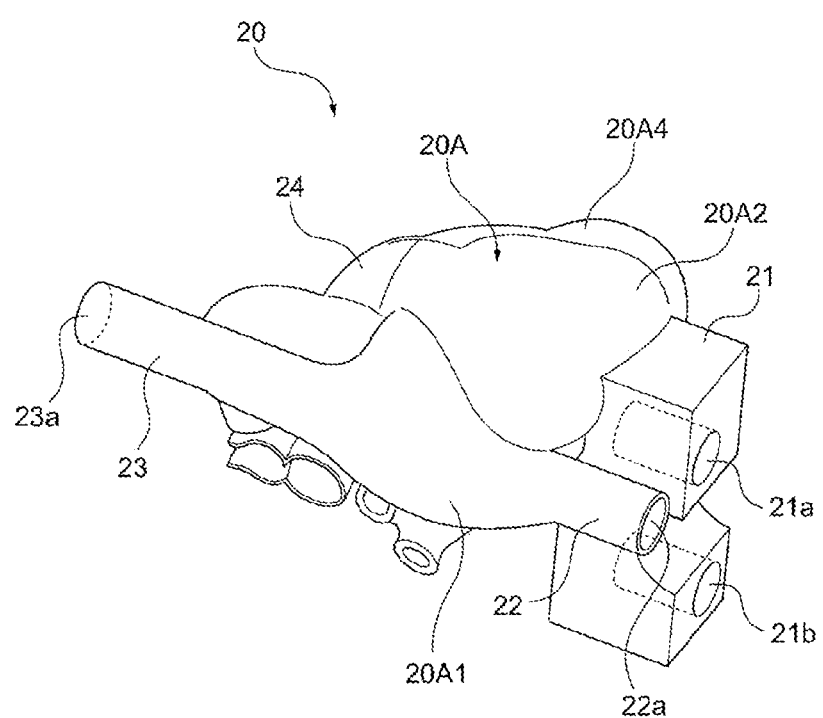
FIG. 3 is a diagram illustrating an example of a right heart model, which is one of the heart models according to the present invention.

As illustrated in FIG. 3, the right heart model 20 of the present embodiment includes a main body 20A simulating the human heart, and in the inside of the main body, a right atrium 20A1, a right ventricle 20A2, a left atrium (not shown in the diagram), and a left ventricle 20A4 are formed similarly to the human heart. Venae cavae (inferior vena cava 22 and superior vena cava 23) are connected to the right atrium 20A1, and a pulmonary artery 24 is connected to the right ventricle 20A2. Since the inferior vena cava 22 and the superior vena cava 23 serve as pathways for catheter introduction, the inferior vena cava 22 and the superior vena cava 23 are formed sufficiently long to the extent that those blood vessels can be connected to the catheter installation parts 11d and 13a formed in the container 10. The respective ends of the inferior vena cava 22 and the superior vena cava 23 are opened (openings 22a and 23a) and are connected to the installation parts 11d and 13a, respectively, that are formed in the container 10, serving as the inlet ports for catheters.

The inferior vena cava 22 reaches to the femoral vein that runs through the inguinal region and serves as a pathway for introduction of a catheter that is introduced through the inguinal region, and the superior vena cava 23 serves as a pathway for introduction of a catheter that is introduced through the internal jugular vein that runs through the base of the neck. In regard to examinations or surgeries of the interior of the heart as an object of simulation using the right heart model 20, the blood vessel through which a catheter is introduced is generally femoral vein, and depending on the conditions of a patient or the like, internal jugular vein may be selected. Therefore, two kinds of pathways for catheter introduction conforming to an actual situation can be selected.

At the caudal side (terminal) of the main body 20A of the right heart model 20, a support unit 21 connected to the container 10 is formed. The support unit 21 does not exist in the human body; however, according to the present embodiment, as illustrated in FIG. 3, the support unit has a shape such as two approximate cuboids connected together. Concavities 21a and 21b formed at an edge of the support unit 21 are connected respectively to holding protrusions 11f and 11g of the connection units 11a and 11c of the container 10, and have a function of stably fixing the right heart model 20 to the container 10. Thereby, the right heart model 20 is retained by the connection units 11a and 11c such that the right heart model 20 floats in the liquid held in the accommodating unit 10a of the container.

As described above, in the case of using the right heart model 20, it is not necessary to circulate the liquid by connecting the pump 60, and it is desirable that the right heart model is filled with the liquid contained in the container 10. Therefore, the concavity 21a of the support unit 21 may not be communicating with the inside of the main body 20A.

Next, the coronary artery model 30 according to the present embodiment will be explained with reference to FIG. 4.

Figure 4:
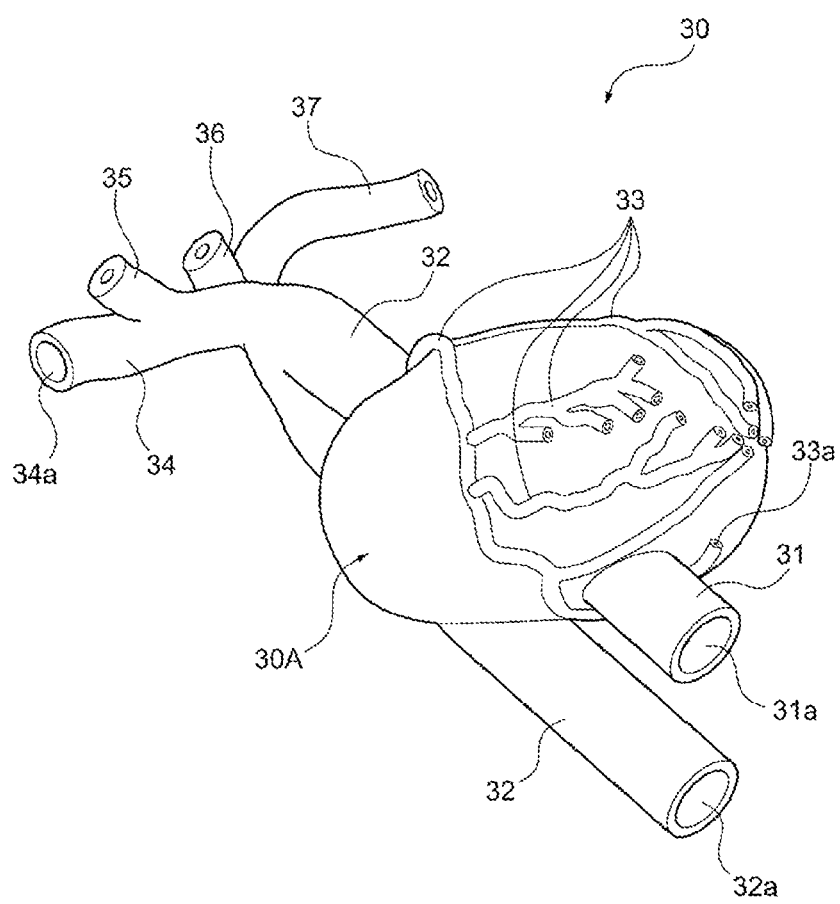
FIG. 4 is a diagram illustrating an example of a coronary artery model, which is one of the heart models according to the present invention.

As illustrated in FIG. 4, the coronary artery model 30 includes a main body 30A simulating the human heart. The human heart includes a right atrium, a right ventricle, a left atrium, and a left ventricle; however, the main body 30A does not include such an internal structure, and the interior is a cavity.

As illustrated in FIG. 4, an aorta 32 is provided on the superior side of the main body 30A, similarly to the human heart. Furthermore, an inflow tube (terminal) 31 is provided at the apex of the heart formed on the caudal side of the main body 30A. The inflow tube 31 does not exist in the human body; however, according to the present embodiment, the inflow tube 31 serves as a pathway through which the liquid (pulsatile flow) sent from the pump 60 (see FIG. 12) flows into the main body 30A. The liquid that has flowed into the main body 30A from the inflow tube 31 passes through the interior of the cavity with certain directionality, and flows out to reach the aorta 32.

On the surface of the main body 30A, a number of coronary arteries 33 having a thin and complicated shape are formed, similarly to the human heart. The coronary arteries 33 are branched from the origin of the aorta 32 and are installed so as to follow the surface of the main body 30A. According to the present embodiment, a discharge port 33a is formed in the end region of the coronary arteries 33, and the liquid that has flowed into the coronary arteries 33 is discharged to the outside (outside of the main body 30A) through the discharge port 33a.

It is preferable that simulating bodies of the blood vessels connected to the aorta in the human body are provided on the pathway of the aorta 32. According to the present embodiment, the simulated blood vessels illustrated in FIG. 4, specifically, right subclavian artery 34, common carotid arteries 35 and 36, and left subclavian artery 37 are provided similarly to the human body. The right subclavian artery 34 is a pathway for introducing a catheter that is introduced through an arm, and the catheter operated by a trainee reaches the aorta 32 from the right subclavian artery 34 and is inserted into the coronary artery 33 that branches from the origin of the coronary arteries. In FIG. 4, the aorta 32 extending on the back side of the main body 30A reaches to the femoral artery that runs through the inguinal region and serves as a pathway for insertion of a catheter that is introduced through the inguinal region.

The coronary artery model 30 described above is retained so as to float in the liquid, as the opening 31a of the inflow tube 31 is connected to the holding protrusion 11f of the connection unit 11a, and also, the opening 32a of the aorta 32 is connected to the holding protrusion 11g of the connection unit 11c. Then, a pulsatile flow is caused to flow into the coronary artery model from an external pump through the inflow tube 31 while in this state.

Figure 5:
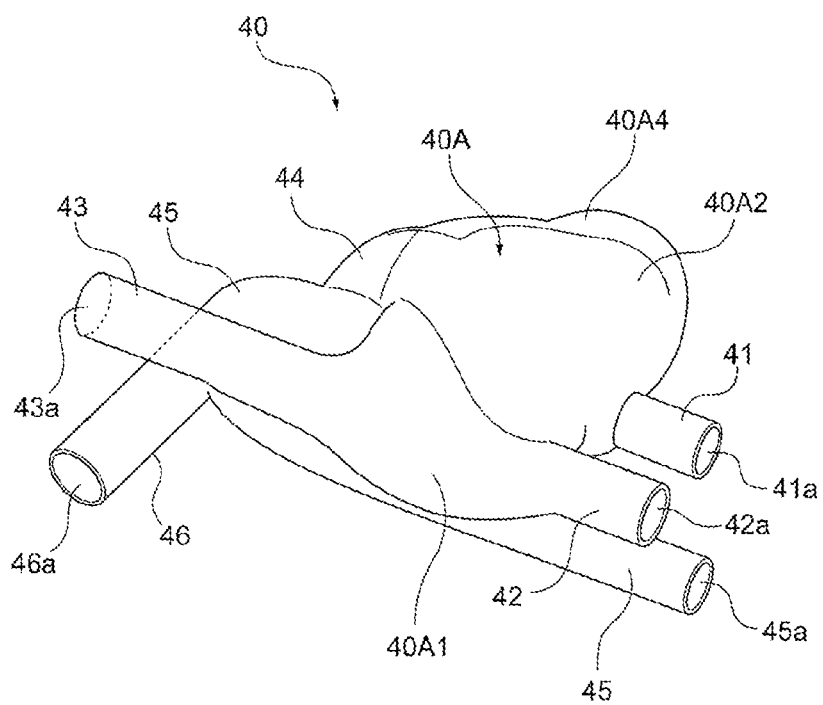
FIG. 5 is a diagram illustrating an example of a TAVI model, which is one of the heart models according to the present invention.

Next, the TAVI model 40 according to the present embodiment will be explained with reference to FIG. 5. As illustrated in FIG. 5, the TAVI model includes a main body 40A simulating the human heart, and in the inside of the main body 40A, a right atrium 40A1, a right ventricle 40A2, a left atrium (not shown in the diagram), and a left ventricle 40A4 are formed. Similarly to the human heart, venae cavae (inferior vena cava 42 and superior vena cava 43) are connected to the right atrium 40A1, a pulmonary artery 44 is connected to the right ventricle 40A2, and an aorta 45 is connected to the left ventricle 40A4. The aorta may include a left subclavian artery 37 and common carotid arteries 35 and 36, similarly to the coronary artery model 30 illustrated in FIG. 4. Furthermore, an aortic valve is disposed at the connection part between the aorta 45 and the left ventricle 40A4; however, it is also possible not to provide a valve there in accordance with the embodiment. Since the aorta 45, the inferior vena cava 42, the right subclavian artery 46, and the superior vena cava 43 serve as pathways for catheter introduction, these blood vessels are formed sufficiently long to the extent that the blood vessels can be connected to the connection unit 11c and the catheter installation parts 11d, 12a, and 13a formed in the container 10. The respective ends of the aorta 45, the inferior vena cava 42, the right subclavian artery 46, and the superior vena cava 43 are opened (openings 45a, 42a, 46a, and 43a), and as illustrated in FIG. 5, the ends are connected to the connection unit 11c and the installation parts 11d, 12a, and 13a and serve as inlet ports for catheters.

As illustrated in FIG. 5, an inflow tube 41 is provided at the apex formed on the caudal side of the main body of heart. The inflow tube 41 does not exist in the human body; however, similarly to the coronary artery model 30 described above, in the present embodiment, the inflow tube 41 serves as a pathway through which the liquid (pulsatile flow) sent from the pump 60 (see FIG. 12) flows into the main body. The liquid that has flowed into the main body through the inflow tube 41 mainly flows into the aorta 45 from the left ventricle 40A4, and a portion thereof flows to the coronary arteries, while the remaining portion flows from the aorta to the common carotid artery, a subclavian artery, or the descending aorta. The diagram simply displays only the part that constitutes the skeleton of the TAVI model; however, as illustrated in FIG. 4, the TAVI model may also include coronary arteries 33, common carotid arteries 35 and 36, and subclavian arteries 34 and 37. Furthermore, at this time, the coronary artery ramification part (entrance) is positioned at the superior side of the aortic valve.

The aorta 45 and the inferior vena cava 42 respectively reach the femoral artery and the femoral vein that run through the inguinal region, and serve as the inlet ports for catheters that are introduced through the inguinal region. The superior vena cava 43 serves as an inlet port for a catheter that is introduced through the internal jugular vein that runs through the base of the neck. In the transcatheter aortic valve implantation as an object of a simulation using the TAVI model 40, the site at which a catheter is introduced is generally femoral artery or the apex of the heart; however, depending on the condition of the patient or the like, a subclavian artery, the femoral vein, or the internal jugular vein may also be selected. Therefore, pathways for catheter introduction conforming to the actual situation can be added. For example, in the case of approach through the apex of the heart, the inflow tube 41 is simultaneously utilized as a pathway for catheter insertion as will be described in detail below; however, at this time, a new catheter installation part may be provided, or a bifurcated tube may be connected, so that a catheter can be inserted while the opening 41a is connected to the pump.

Figure 6:
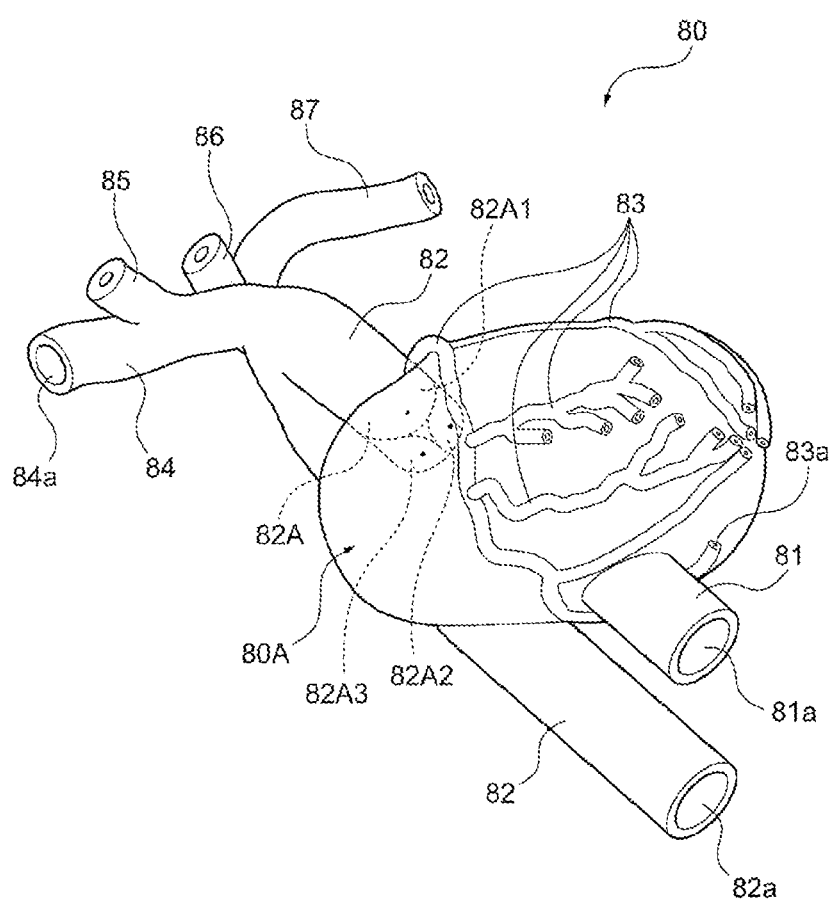
FIG. 6 is a diagram illustrating another example (second embodiment) of the TAVI model, which is one of the heart models according to the present invention.

FIG. 6 is a diagram explaining another embodiment of the TAVI model (TAVI model 80 as a second embodiment).

As illustrated in FIG. 6, in the TAVI model 80, a right atrium, a right ventricle, a left atrium, and a left ventricle are not formed inside the main body 80A that simulates the human heart, and the interior is a cavity. When the interior of the main body 80A is made into a cavity, there is an advantage that the main body 80A is made easy to pulsate due to the pulsatile flow that has flowed in from the pump 60, similarly to the coronary artery model 30 described above. Since a catheter travels only through the inside from the left ventricle to the aorta, and it is not a simulation in which the catheter travels through the inside of the other chambers such as aright atrium, a right ventricle, and a left atrium, there is no serious problem even if these partitions, namely, an interatrial septum, an interventricular septum, a tricuspid valve, and a mitral valve are not formed inside the main body 80A. It is possible to perform a simulation by diagnosing the integrated cavity as the left ventricle.

Similarly to the human heart, an aorta 82 is provided at the superior side of the main body 80A. This aorta 82 protrudes to the interior of the main body 80A through the superior side of the main body 80A, and an aortic valve 82A is formed at the end of the aorta 82 similarly to that in the human body. The aortic valve 82A is positioned at the boundary between the aorta 82 and the left ventricle in the human body; however, in the present embodiment, since a left ventricle is not formed, the aorta 82 protrudes into the inside of the main body 80A to the vicinity of a position that is assumed to be the right position in the case where there is a left ventricle, and the aortic valve 82A is formed at the end of the aorta.

The aortic valve 82A has three valve cusps such as a right coronary cusp 82A1, a left coronary cusp 82A2, and a non-coronary cusp 82A3, similarly to the human body. The aortic valve 82A has a shape in which these three valve cusps are connected at the bottom such as in the case of petals, and the respective valve cusps 82A1, 82A2, and 82A3 are formed in a rounded petal-like form. The bottoms of the various valve cusps are marked with point marks of three different colors (red, yellow, and green), and the valve cusps and the colors are in 1:1 correspondence according to common knowledge of medical professionals. These point marks serve as markers when simulation is performed by introducing a catheter under visual inspection. Furthermore, when a radio-opaque material is used for these point marks, the point marks can also be used as markers when simulation is performed as so-called as opaque markers, even under X-ray illumination. Meanwhile, the shape of the marker may be any shape as long as the marker can be recognized as a marker, and the shape is not limited to a point mark as shown in the diagram. In addition to the bottoms of the various valve cusps, the annulus part may also be treated in the same manner and can be utilized as a marker. By using a radio-opaque material also for this part, the calcified condition that is observed in many cases of aortic valve stenosis can be reproduced.

Furthermore, the apex of the heart formed at the caudal side of the main body 80A is provided with an inflow tube (terminal) 81. The inflow tube 81 does not exist in the human body; however, according to the present embodiment, the inflow tube serves as a pathway through which a liquid (pulsatile flow) sent from the pump 60 flows into the main body 80A. On the surface of the main body 80A, coronary arteries 83 are formed similarly to the human heart, and it is also possible to perform a simulation similar to that for the coronary artery model 30 described above. The coronary arteries 83 may not be formed because the coronary arteries are not essential for the simulation of transcatheter aortic valve implantation using a TAVI model of the like; however, it is desirable that the coronary arteries 83 are available. In the transcatheter aortic valve implantation, coronary artery occlusion may occur as a disease complication, and thus, during a relevant surgery, the condition of occlusion may be checked by performing coronary arteriography.

It is preferable that simulating bodies of the blood vessels connected to the aorta in the human body are provided on the pathway of the aorta 82. According to the present embodiment, the simulated blood vessels illustrated in FIG. 6, specifically, right subclavian artery 84, common carotid arteries 85 and 86, and left subclavian artery 87 are provided similarly to the human body. In FIG. 6, the aorta 82 extending on the back side of the main body 80A reaches to the femoral artery that runs through the inguinal region, and serves as a pathway for introduction of a catheter that is introduced through the inguinal region. In the case of approach through the apex of the heart, a catheter is introduced through the opening 81a of the inflow tube 81. In this case, the opening 81a serves as an inflow port for the pulsatile flow sent from the pump 60 as described above, and also serves as a port for catheter introduction in the approach through the apex of the heart.

In regard to the TAVI model 40 of FIG. 5 or the TAVI model 80 of FIG. 6, a stent valve place therein can be made easily removable through the apex side of the heart, by making the diameter of the openings 41a and 81a of the inflow tubes larger than those of the coronary artery model (opening 31a of the inflow tube of FIG. 4).

FIG. 7A, FIG. 7B, FIG. 8A and FIG. 8B are diagrams illustrating another embodiment of the TAVI model (TAVI model 100 as a third embodiment).

Figure 7A:
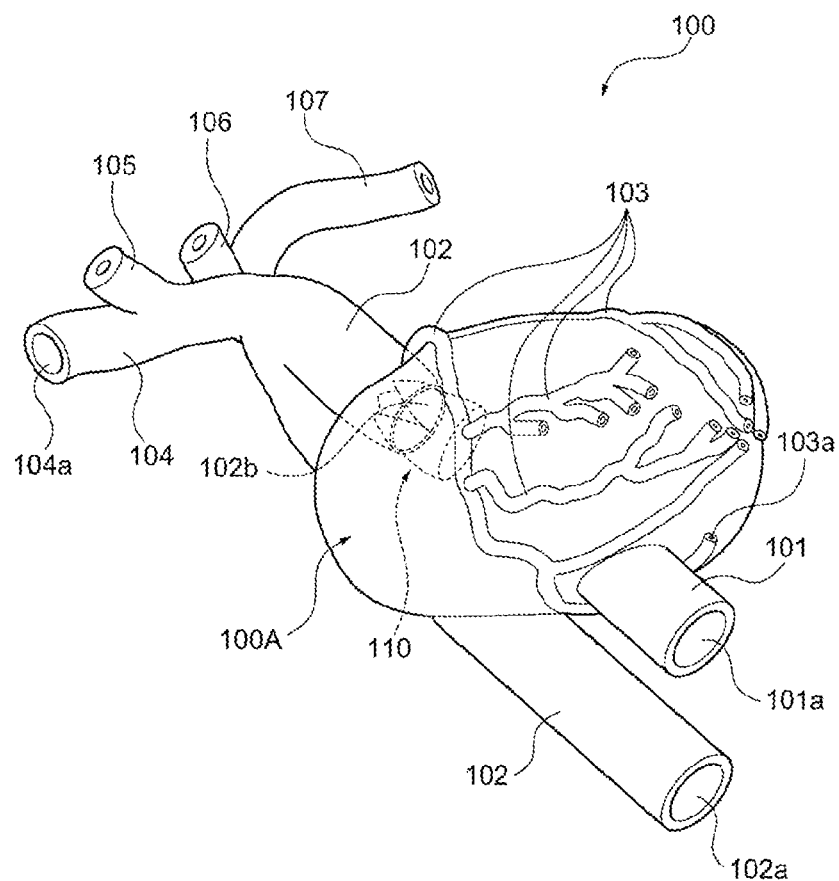
FIGS. 7A and 7B are a set of diagrams illustrating another example (third embodiment) of the TAVI model, which is one of the heart models according to the present invention.
Figure 7B:
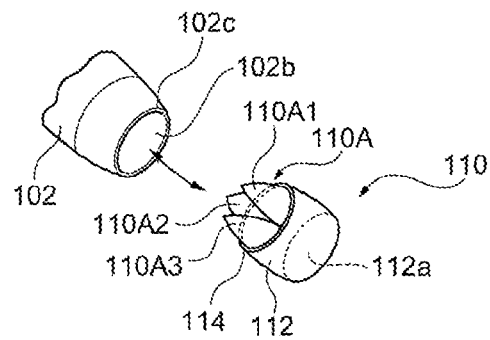

As illustrated in FIGS. 7A and 7B, in the TAVI model 100, similarly to the TAVI model 80 described above, a right atrium, a right ventricle, a left atrium, and a left ventricle are not formed inside the main body 100A that simulates the human heart, and the interior is a cavity. When the interior of the main body 100A is made into a cavity, there is an advantage that the main body 100A is made easy to pulsate due to the pulsatile flow that has flowed in from the pump 60. Since a catheter travels only through the inside from the left ventricle to the aorta, and it is not a simulation in which the catheter travels through the inside of the other chambers such as a right atrium, a right ventricle, and a left atrium, there is no serious problem even if these partitions, namely, an interatrial septum, an interventricular septum, a tricuspid valve, and a mitral valve are not formed inside the main body 100A. It is possible to perform a simulation by diagnosing the integrated cavity as the left ventricle.

Similarly to the human heart, an aorta 102 is provided at the superior side of the main body 100A. This aorta 102 protrudes to the interior of the main body 100A through the superior side of the main body 100A, and an opening 102b is formed at the end of the aorta 102. A detachable aortic valve 110 is mounted in the opening 102b. The aortic valve 110 is positioned at the boundary between the aorta 102 and the left ventricle in the human body; however, in the present embodiment, since a left ventricle is not formed, it is configured such that the aorta 102 protrudes into the inside of the main body 100A to the vicinity of a position that is assumed to be the right position in the case where there is a left ventricle, and the aortic valve 110 is formed at the end of the aorta.

In the human body, the aortic valve is integrally connected to the end of the aorta similarly to the TAVI model 80 of the second embodiment; however, in the TAVI model 100 of the present embodiment, the aortic valve 110 is formed separately from the other parts, and the aortic valve is detachable and reattachable. Therefore, when aortic valves 110 conforming to various symptoms and conditions intrinsic to patients are prepared, various simulations concerning the aortic valve can be conveniently carried out simply by replacing the aortic valve 110 only. In the case of the TAVI model 80, a plurality of TAVI models as a whole needs to be formed in accordance with different aortic valves, and at the time of installation, it is also necessary to switch the entire models. However, in the case of the TAVI model 100, only a plurality of aortic valves may be prepared, and even at the time of installation, only the aortic valves may be detached and switched. It is efficient from the viewpoints of production cost, operation efficiency, and large storage spaces.

Furthermore, by making the aortic valve 110 detachable, as will be described below, a stent valve (artificial valve-attached stent) placed in the aortic valve 110 can be easily removed at the time of completion of the simulation. Hereinafter, the aorta 102 and the aortic valve 110 that is detached from and attached to the aorta will be explained with reference to FIG. 7B to FIG. 9.

As illustrated in FIG. 7B, the aortic valve 110 includes a valve cusp unit 110A including various valve cusps such as a right coronary cusp 110A1, a left coronary cusp 110A2, and a non-coronary cusp 110A3 simulating the aortic valve in the human body; an annular annulus part 114 present at the bottom of the valve cusp unit 110A at which these valve cusps are connected in a petal-like form; and a cylindrical-shaped left ventricle outflow path part 112 connected to the annulus part 114 and serves as a handle for the user at the time of attachment and detachment. The aortic valve 110 is inserted into the inside of the main body of heart 100A through the opening 101a of the inflow tube, with the valve cusp unit 110A being arranged to head forward, and is inserted into the opening 102b of the aorta. After the insertion, the annulus part 114 is connected to the periphery 102c of the opening 102b, and thereby, the aortic valve 110 is fixed and mounted at the end of the aorta 102.

Figure 8A:
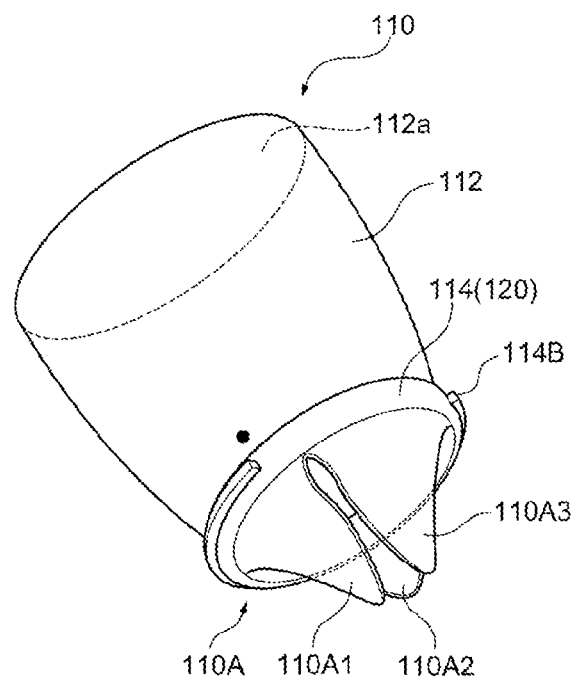
FIG. 8A is a magnified view of the detached aortic valve in the TAVI model of FIGS. 7A and 7B.
Figure 8B:
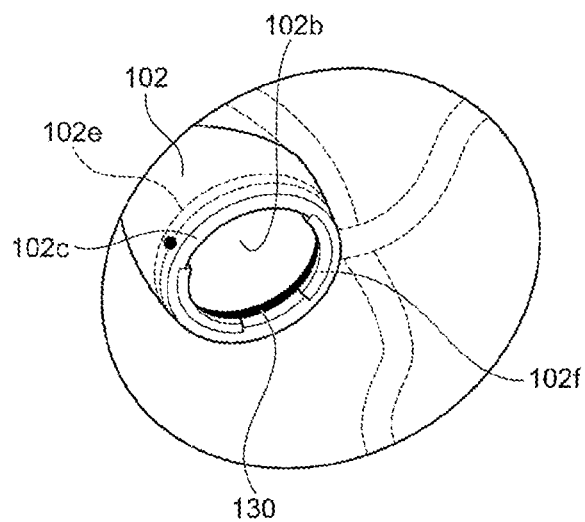
FIG. 8B is a perspective view showing the interior of the TAVI model from the opening of the inflow tube, and is a magnified view of the vicinity of the opening of the aorta.

Here, as will be described below, the annulus part 114 and the periphery 102c of the opening 102b form a structure in which the annulus part 114 and the periphery 102c are connected such that the protrusion 114B of the inner ring 120 and the protrusion 102B of the outer ring 130 to which the annulus part 114 and the periphery 102c are adhered are overlapped in a rotating manner. Therefore, at the time of insertion, there is a need to insert the aortic valve such that the protrusion 114B on the annulus part 114 side is not brought into contact with the protrusion 102B formed on the inner surface on inner side of the aorta 102. As illustrated in FIGS. 8A and 8B, the aortic valve 110 can be inserted in a right direction by attaching markers (black circles in the diagram) to the outer surfaces of the aortic valve 110 and the aorta 102, and inserting the aortic valve so as to fit the black circle marks in line; or by forming a protrusion 102f on the periphery 102c, and inserting the aortic valve such that the protrusion 114B is not brought into contact with this protrusion 102f.

Next, the structure in which the annulus part 114 is connected to the opening periphery 102c of the aorta will be explained with reference to FIG. 8A, FIG. 8B and FIG. 9. On the outer circumference of the annulus part 114, an inner ring 120 is fixed, and on the inner circumferential surface on the inner side of the periphery 102c of the opening 102b of the aorta 102, an outer ring 130 is fixed. The inner ring 120 has an annular parent body 120A; and a protrusion 114B that is formed on the outer circumference of the parent body 120A and has an approximately rectangular-shaped cross-section. The inner ring 120 is adhered and fixed on the outer side of the annulus part 114 of the aortic valve 110. The protrusion 114B is formed in the lower part on the outer circumference of the parent body 120A at two sites that face each other, to a length equivalent to a central angle of about 80°, and one of the ends of the protrusion 114B includes a convexity 114D and a concavity 114E that are successively formed in the circumferential direction as illustrated in the diagram. Meanwhile, the outer ring 130 has an annular parent body 130A; and a protrusion 102B that is formed along the inner circumference of the parent body 130A and has an approximately rectangular-shaped cross-section, and the outer ring 130 is fixed on the inner circumferential surface on the inner side of the periphery 102c of the opening 102b of the aorta 102. The protrusion 102B is formed at the top of the inner circumference of the parent body 130A at two sites that face each other, to a length equivalent to a central angle of about 90°, and one of the ends of the protrusion 102B includes a convexity 102E as illustrated in the diagram.

Regarding the outer ring 130, a circumferential groove 102e is formed on the inner circumferential surface on the inner side of the periphery 102c of the opening 102b of the aorta 102, and the outer ring 130 is embedded in that part. In this case, the outer ring 130 is formed from a hard resin that is harder than the material for the aorta 102 (for example, an epoxy-based or urethane-based hard resin). As such, by embedding a hard outer ring 130 therein, when the aortic valve 110 is connected to the aorta 102, effects of preventing deformation of the opening portion and making it difficult for the two elements to come off from each other are provided.

Next, a method of engaging the inner ring 120 fixed on the outer side of the aortic valve 110 with the outer ring 130 fixed on the inner side of the opening 102c of the aorta by rotating the ring will be explained. As indicated by the dotted arrow in FIG. 9, when the protrusion 114B of the inner ring 120 is inserted into the protrusion 102B of the outer ring such that the protrusions do not overlap on the circumference, and the rings are rotated clockwise for about 90°, the protrusion 114B is positioned below the protrusion 102B. Here, on the inner circumferential surface of the parent body 130A of the outer ring, a stopping tool 130B is formed at a position slightly separated apart from the convexity 102E along the circumferential direction, and it is designed such that the protrusion 114B is stopped by this stopping tool at a position at which the inner ring 120 has rotated for about 90°. At that time, the concavity 114E at the end of the protrusion 114B is engaged with the convexity 102E of the protrusion 102B, and the convexity 114D at the end of the protrusion 114B is fixed in the gap between the convexity 102E of the protrusion 102B and the stopping tool 130B.

As such, when a convexity and a concavity are connected by engagement and fixed, stability of the aortic valve mounted can be enhanced. Since the part at which the aortic valve 110 and the aorta 102 are engaged may be pushed by a catheter that is inserted, or may be subjected to the pressure of the pulsatile flow that flows in from the pump, it is preferable that the connection is stabilized. Furthermore, it is preferable that when the aortic valve 110 is mounted and fixed, the fixing position in the circumferential direction of the inner ring 120 with respect to the annulus part 114, and the fixing position in the circumferential direction of the outer ring 130 with respect to the inner circumferential surface on the inner side of the periphery 102c of the opening 102b of the aorta 102 are designed such that the positions of the various valve cusps mentioned above (right coronary cusp 110A1, left coronary cusp 110A2, and non-coronary cusp 110A3) are similar to the corresponding positions in the human body. In the present embodiment, the length in the circumferential direction of the protrusions 114B and 102B is a portion of the circumference equivalent to a central angle of 80° to 90°, and the number of protrusions is two each on the circumference. However, there are no particular limitations on the length or the number, and as described above, a structure in which the protrusion 102B and the protrusion 114B overlap each other at the time of mounting the aortic valve is desirable.

Figure 9:
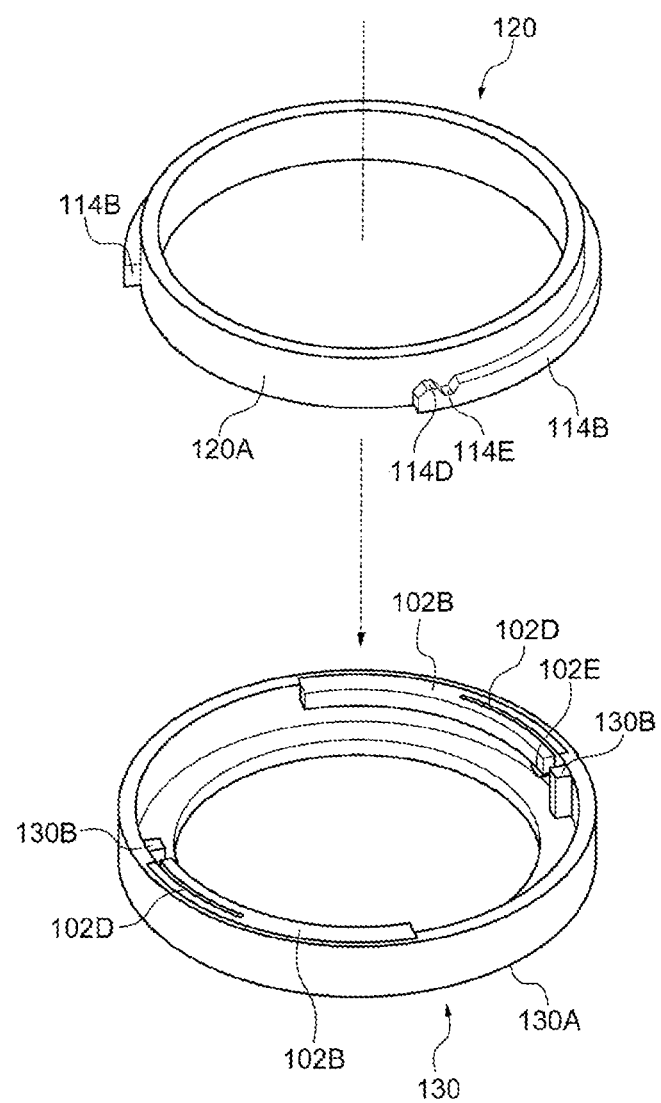
FIG. 9 is a diagram illustrating the essential part of the connection structure between the aortic valve and the aorta illustrated in FIGS. 8A and 8B.

A slit 102D is provided in a portion of the continuation part of the protrusion 102B and the parent body 130A, and thereby, when the convexity 114D is brought into contact with the convexity 102E, the convexity 102E is made to be slightly lifted up (in the upper direction of FIG. 9). Therefore, the convexity 114D is configured so as to rotate even after the contact with the convexity 102E, displace an end of the protrusion 102B, and then reach the stopping tool 130B disposed in front. Thereby, a user can be made to have a moderation feeling at the time of mounting the aorta, and can be made to comprehend the accurate position of mounting.

It is preferable that the inner ring 120 or the outer ring 130 is subjected to coloring. Thereby, when the aortic valve 110 is attached or detached, the coloration serves as a marker for position adjustment to a predetermined position of the aorta, and also, the coloration can serve as the reference for position when a catheter is introduced under visual inspection, and placement of a stent valve is simulated. When a radio-opaque material is used for the colored portion, even under X-ray illumination, the coloration serves as a marker when a simulation is performed using a so-called radio-opaque marker. A colored or radio-opaque material may also be used in the annulus part 114 and the protrusion 114B of the aortic valve 110, instead of the peripheral edge 102c and the opening 102b. In regard to aortic valve stenosis and the like that require a catheter procedure that becomes an object of simulation of the TAVI model, usually, since the annulus part of a patent is in a calcified condition and is therefore radio-opaque, a condition similar to the human body can be reproduced thereby. Furthermore, also for the valve cusp unit 110A and the aorta 102, a calcified condition similar to that of the human body can be reproduced by applying a substance having radio-opacity on the surface of the valve cusp unit or the aorta, or imparting radio-opacity to the material that forms the annulus part 114, and a simulation under X-ray illumination can be carried out in an environment closer to the reality. Examples of such radio-opaque material include hydroxyapatite, and substances containing a calcium component or a metal component.

Figure 10:
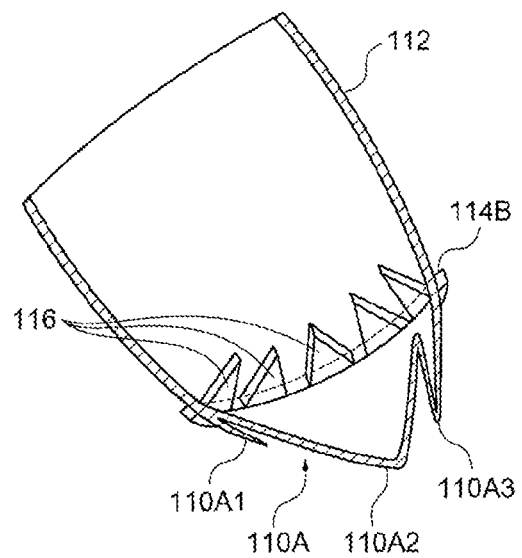
FIG. 10 is a cross-sectional view illustrating an embodiment of the aortic valve of FIG. 8A equipped with a support unit in the inside.

FIG. 10 shows an embodiment including a placing part (concavities and convexities that enhance the frictional force at the surface) 116 inside the aortic valve 110. In this embodiment, as illustrated in the diagram, a number of approximately triangular-shaped placing parts 116 are formed along the inner circumference of the annulus part 114 on the inner wall of the annulus part 114 of the aortic valve 110. The placing part 116 does not exist in the human body; however, there is an advantage that a stent valve placed by a catheter operation can be reliably fixed and supported. Specifically, since the aortic valve of a patient who is subjected to a surgical operation of stent valve placement or the like has a surface roughened by calcification or the like, or the hardness of the valve itself is high, the stent valve is easily fixed; however in a simulation using a heart model, since the surface of the aortic valve is smooth, and the hardness of the valve itself is also not so high, there are occasions in which a stent valve placed therein may slip and move along the flow of the pulsatile flow. Such a problem can be solved by forming, on the inner wall of the aortic valve 110, the placing part 116 that increase the surface frictional force to a higher level than that of the inner wall.

As illustrated in FIG. 7A, an inflow tube (terminal) 101 is provided at the apex of the heart formed on the caudal side of the main body 100A. The inflow tube 101 does not exist in the human body; however, in the present embodiment, the inflow tube serves as a pathway through which a liquid (pulsatile flow) sent from the pump 60 flows into the main body 100A. On the surface of the main body 100A, coronary arteries 103 are formed similarly to the human heart, and a simulation similar to the case of the coronary artery model 30 described above can also be carried out. The coronary arteries 103 may not be formed because they are not essential for the simulation of transcatheter aortic valve implantation by means of a TAVI model or the like; however, it is desirable that the coronary arteries are available. In the transcatheter aortic valve implantation, coronary artery occlusion may occur as a disease complication, and thus, during a relevant surgery, the condition of occlusion may be checked by performing coronary arteriography. Furthermore, a countermeasure can be taken upon occlusion, by having a guide wire inserted in the coronary arteries in advance.

It is preferable that the inner diameter of the inflow tube 101 is formed to be larger than the outer diameter of the aortic valve 110. Thereby, when the aortic valve 110 having a stent valve placed therein is taken out, the aortic valve 110 can easily pass through the inside of the inflow tube 101 that serves as a pathway for the aortic valve. It is preferable that the aortic valve 110 has a size simulating the aortic valve in the human body, and it is preferable that the inner diameter of the inflow tube 101 is adjusted to be larger than the outer diameter of the aortic valve 110.

It is preferable that simulating bodies of the blood vessels connected to the aorta in the human body are provided on the pathway of the aorta 102 described above. According to the present embodiment, the simulated blood vessels illustrated in FIG. 7A, specifically, right subclavian artery 104, common carotid arteries 105 and 106, and left subclavian artery 107 are provided similarly to the human body. In FIG. 7A, the aorta 102 extending on the backside of the main body 100A reaches to the femoral artery that runs through the inguinal region, and serves as a pathway for introduction of a catheter that is introduced through the inguinal region. In the case of approach through the apex of the heart, a catheter is introduced through the opening 101a of the inflow tube 101. In this case, the opening 101a serves as an inflow port for the pulsatile flow sent from the pump 60 as described above, and also serves as a port for catheter introduction in the approach through the apex of the heart.

In regard to a simulation using the TAVI model 40, 80 or 100 described above, regarding the stent valve placed in the aortic valve, a system which is formed from a shape memory alloy and is placed by extending at a temperature close to the body temperature (near 30° C. to 40° C.) may be employed. In this case, a simulation similar to an actual surgery can be carried out by imparting a function of a constant temperature chamber capable of maintaining the temperature of the container 10 to the same extent as the body temperature of human being (a heater installed in the container 10, or the like).

Figure 11:
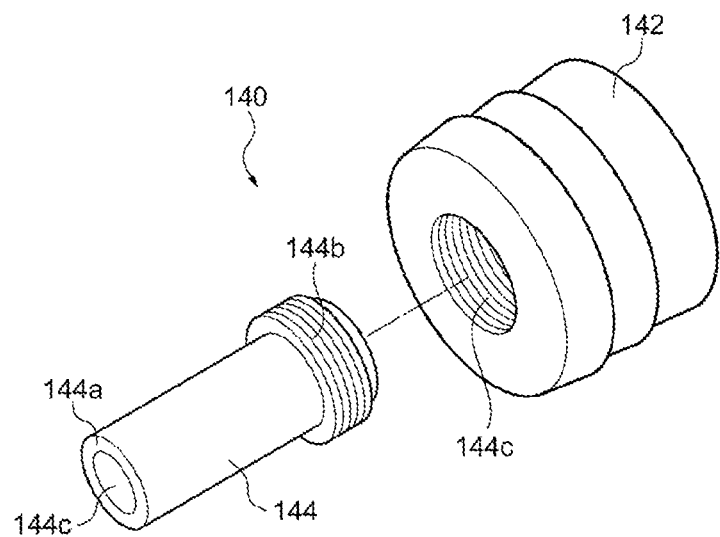
FIG. 11 is a perspective view of an extension member that can be used together with the TAVI model of the second and third embodiments.

In the case of using the TAVI model 80 or 100, since the interior of the main body of heart 80A or 100A is a cavity, the pulsatile flow that has flowed in from the pump 60 is spread in the inside of the main body of heart, and it may be difficult for the pulsatile flow to be concentrated on the aortic valve 82A (110). Next, an extension member 140 that solves this problem will be explained. FIG. 11 is a perspective view of an extension member 140, and the extension member 140 has a cylindrical-shaped extension unit 144; and a cylindrical-shaped base 142 that is screw-engaged with the extension unit 144 and is also connected to the holding protrusion 11f of the container 10 and the inflow tube 81 (101) of the TAVI model 80 (100). As illustrated in the diagram, the base 142 has surface concavities and convexities on the outer circumferential surface, and is configured not to be easily detached when being inserted into the inflow tube 81 (101).

In the interior of the base 142, an opening 142c that penetrates through the interior and includes an inner wall having thread grooves formed thereon, is formed. Screw threads are formed at one end 144b of the extension unit 144, and the base 142 and the extension unit 144 are connected as these screw threads are engaged by rotation with the thread grooves of the opening 142c. A through-hole 144c is formed inside the extension unit 144, and when the base 142 and the extension unit 144 are connected, this opening 144c and the above-mentioned opening 142c are in communication.

When the base 142 and the extension unit 144 are connected as such, and then the extension member 140 is connected to the holding protrusion 11f, and subsequently the inflow tube 81 (101) is mounted on the outside of the base 142, the pulsatile flow sent out from the pump 60 passes through the opening 144c via the opening 142c and then is discharged through the other end 144a of the extension unit 144 to flow into the main body of heart 80A (100A) of the TAVI model 80 (100). That is, the inflow port for the pulsatile flow in the main body of heart 80A (100A) is brought closer to the aortic valve 82A (110) since the inflow port moves from the end of the inflow tube 81 (101) to the end 144a by using the extension member 140. As the inflow port for the pulsatile flow that flows into the heart model is brought closer to the aortic valve 82A (110), the pulsatile flow can be concentrated on the aortic valve 82A (110) without having the pulsatile flow spread.

The position of the end 144b in the opening 142c can be adjusted by screw-engagement, and the system is configured such that the position of the inflow port (opening 144c) for the pulsatile flow that flow into the heart model can be varied thereby. As a result, the position of the opening 144c can be adjusted depending on the size of the TAVI model used for the simulation, the pressure of the pulsatile flow, or the like, and the degree of concentration of the pulsatile flow on the aortic valve 82A (110) can be optimized.

Figure 12:
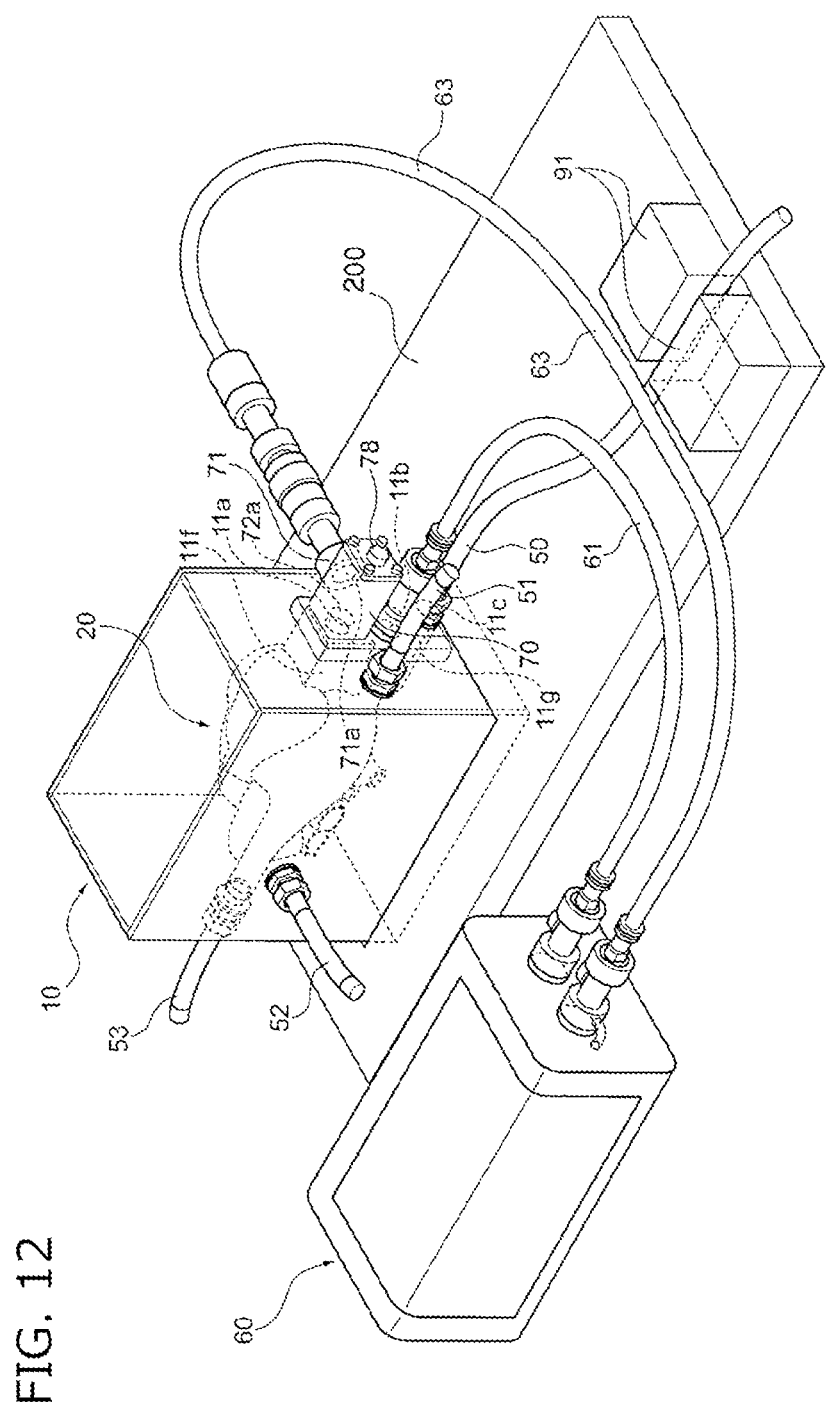
FIG. 12 is a general schematic view illustrating one use embodiment of the container for a catheter simulator according to the present invention.

FIG. 12 is a diagram illustrating a use embodiment of the container 10 for a catheter simulator equipped with a two-way cock 70. In a case in which the approach through the apex of the heart is simulated with the various TAVI models, as illustrated in FIG. 12, a tube that is bifurcated (two-way cock 70) may be connected to the connection unit 11a of the container 10. Thereby, inflow of a pulsatile flow and introduction of a catheter can be realized by means of a single opening 41a, 81a or 101a. In FIG. 12, the container 10 is connected to the pump 60 through a supply tube 63 and a discharge tube 61, and the two-way cock 70 is disposed between the supply tube 63 and the connection unit 11a of the container.

As illustrated in FIG. 12, the container 10 may be installed on a fixing base 200. Depending on the catheter, guide wire, and other devices that are inserted, the container 10 moves due to the pressure applied by the trainee at the time of insertion of these devices, and therefore, such a situation can be prevented by fixing the container on the fixing base 200. The fixing base 200 is desirably formed from a material having a strength that is sufficient for holding and fixing of the container 10 and having resistance to the liquid that fills the container 10 (a hardened urethane foam or the like). The shape is not particularly limited as long as the fixing base has stability; however, in a case in which the fixing base has a plate shape as shown in FIG. 12, the container 10 can be installed by forming a depression on the plate surface. Thereby, the container 10 filled with a liquid serves as a weight, the fixing base 200 does not easily move, and a stabilized operation is enabled. Furthermore, a fixing unit 91 that sandwiches and fixes the pathway for catheter introduction may also be formed on the fixing base 200. Thereby, it becomes easier to apply pressure at the time when the trainee inserts a catheter or the like.

Also, for the same reasons, there are occasions in which the heart model installed inside the container 10 comes off from the holding protrusions 11f and 11g of the container 10. In that case, the above-described situation can be prevented by connecting the heart model to the holding protrusions 11f and 11g and then reinforcing the connection by means of a fixing ring (not shown in the diagram), or by fixing the heart model by means of a retention base (not shown in the diagram).

Figure 13:
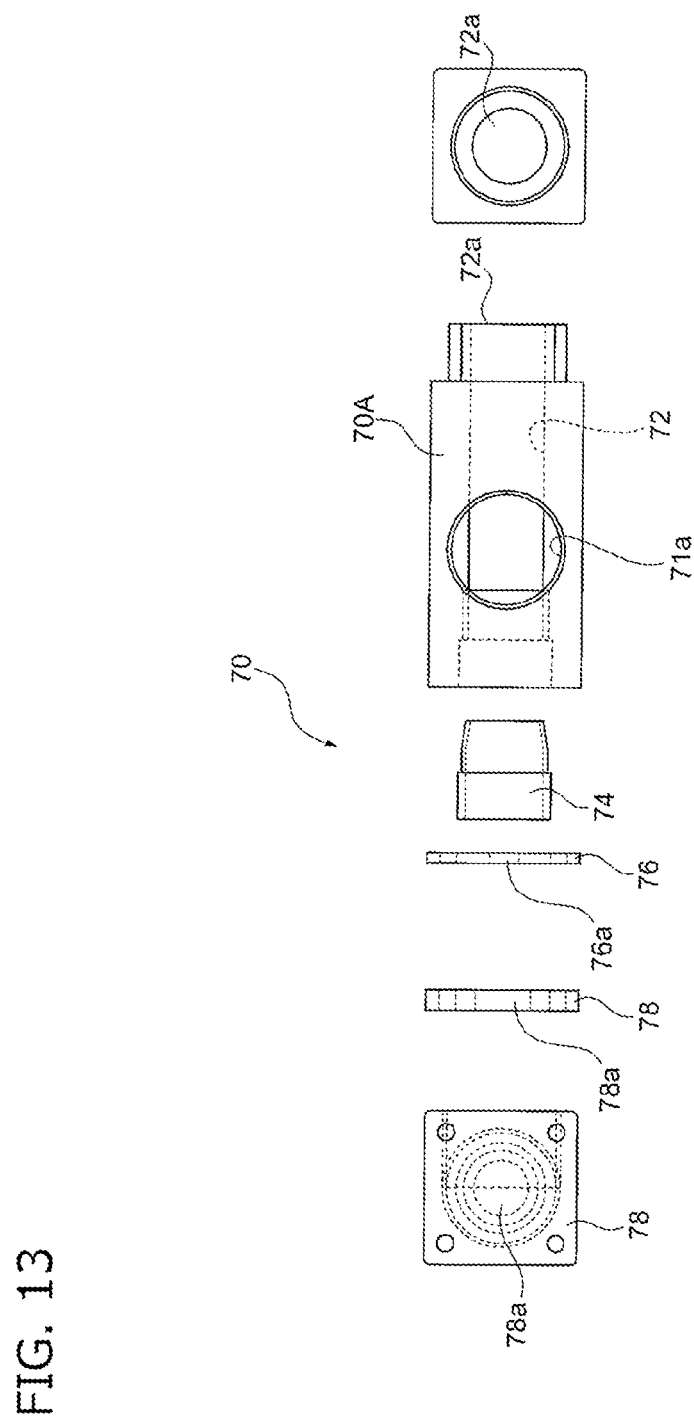
FIG. 13 is an exploded view of a two-way cock installed in the container of a catheter simulator illustrated in FIG. 12.

Next, the two-way cock 70 will be explained with reference to FIG. 13 and FIG. 14. The main body 70A of the two-way cock 70 has an inflow tube 71 through which a liquid (pulsatile flow) flows in from the pump 60; a pathway for catheter introduction 72; a duckbill valve 74 that is installed in the pathway for catheter introduction 72 and functions as a one-way valve; a silicone rubber gasket 76 adjoining the duckbill valve 74; and an end-plate 78 that adjoins the silicone rubber gasket 76 and includes a port for catheter introduction 78a through which a catheter is inserted from the outside. The inflow tube 71 is installed so as to orthogonally intersect the pathway for introduction 72, and the opening 71a of the inflow tube 71 communicates with the interior of the pathway for catheter introduction 72 on the downstream side of the duckbill valve 74. Therefore, a pulsatile flow that has passed through the inflow tube 71 flows into the pathway for introduction 72 through the opening 71a. It is desirable as long as the inflow tube 71 is installed in the pathway for introduction 72 so as to communicate with the interior of the pathway for catheter introduction 72 on the downstream side of the duckbill valve 74, and it is not necessarily essential that the inflow tube 71 is installed so as to orthogonally intersect the pathway for introduction 72.

At one end 72a of the pathway for introduction 72, screw-like concavities and convexities are formed, and thus the one end 72a is connected to the connection unit 11a of the container 10 by screw-engagement. Thereby, the liquid that has flowed into the pathway for introduction 72 from the inflow tube 71, flows into the TAVI model 40, 80 or 100 inside the container 10 through the one end 72a.

In the interior of the pathway for introduction 72, the duckbill valve 74 and the silicone rubber gasket 76 are installed between the site where the inflow tube 71 is perpendicularly installed and the end-plate 78. The duckbill valve 74 allows insertion of a catheter when opened, and the silicone rubber gasket 76 has an opening 76a formed therein, through which a catheter is inserted. These accomplish the role of permitting insertion and extraction of a catheter, while functioning as a check valve so that the liquid that has flowed into the pathway for introduction 72 does not leak to the outside of the port for catheter introduction 78a.

Since the duckbill valve 74 has a cross-section that resembles the beak of a bird, when a catheter having an approximately circular-shaped cross-section is introduced, there occurs a gap between the two elements, and at this time, the liquid of the inflow tube 71 leaks out through the duckbill valve 74. By preventing flowing out of this leaked liquid with the silicone rubber gasket 76, the duckbill valve and the silicone rubber gasket can be made to function as a check valve so that the liquid that has flowed into the pathway for introduction 72 does not leak to the outside through the port for catheter introduction 78a. Specifically, when the diameter of the hole for catheter penetration 76a formed in the silicone rubber gasket 76 is designed to be smaller than the diameter of the catheter, the catheter can be caused to adhere closely to the hole for penetration 76a, and thereby a gap can be eliminated. Thus, the liquid that has leaked from the duckbill valve 74 can be prevented from flowing out by means of the silicone rubber gasket 76.

Meanwhile, when the catheter is pulled out after completion of the simulation, since the duckbill valve 74 is automatically closed by the liquid pressure inside the pathway for catheter introduction 72, the liquid inside the pathway for catheter introduction 72 is blocked by the duckbill valve 74, and as a result, the system is maintained in a state in which liquid outflow to the outside through the port for catheter introduction 78a is restricted. As a mechanism for preventing liquid outflow, it is also acceptable to have a lid or stopper attached to the part of the port for catheter introduction 78a.

In regard to the two-way cock 70, in a case in which the catheter insertion-extraction part coincides with the inflow port from the pump 60, it is desirable that the two-way cock 70 has a check valve structure that allows insertion of a catheter into a heart model and prevents the liquid transported from the pump 60 from leaking to the catheter insertion side. In regard to the main body of valve that is installed inside, or the mechanism of preventing liquid leakage, modification can be applied as appropriate by, for example, using a cross slit valve.

Figure 14:
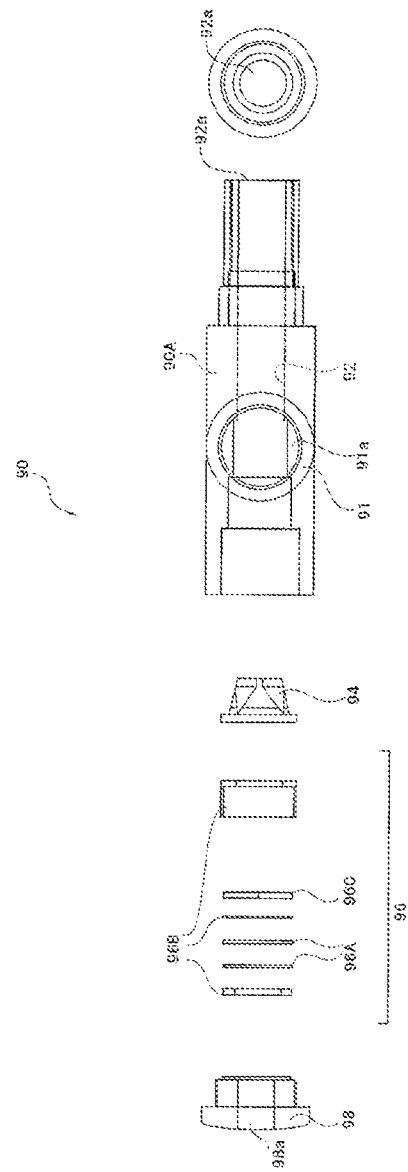
FIG. 14 is an exploded view of another embodiment of the two-way cock.

FIG. 14 illustrates an example of using a cross slit valve 94 in the two-way cock 90. The main body 90A of the two-way cock 90 has an inflow tube 91 through which a liquid (pulsatile flow) flows in from the pump 60; a pathway for catheter introduction 92; a cross slit valve 94 made of silicone, which is installed in the pathway for catheter introduction 92 and functions as a one-way valve; a valve unit 96 that adjoins the cross slit valve 94; and an end-plate 98 that adjoins the valve unit 96 and includes a port for catheter introduction 98a through which a catheter is inserted from the outside. The inflow tube 91 is installed so as to orthogonally intersect the pathway for introduction 92, and the opening 91a of the inflow tube 91 communicates with the interior of the pathway for catheter introduction 92 on the downstream side of the cross slit valve 94. Therefore, a pulsatile flow that has passed through the inflow tube 91 flows into the pathway for introduction 92 through the opening 91a. It is desirable as long as the inflow tube 91 may be installed in the pathway for introduction 92 so as to communicate with the interior of the pathway for catheter introduction 92 on the downstream side of the cross slit valve 94, and it is not necessarily essential that the inflow tube 91 is installed so as to orthogonally intersect the pathway for introduction 92.

At one end 92a of the pathway for introduction 92, screw-like concavities and convexities are formed, and thus the one end 92a is connected to the connection unit 11a of the container 10 by screw-engagement. Thereby, the liquid that has flowed into the pathway for introduction 92 from the inflow tube 91, flows into the TAVI model 40, 80 or 100 inside the container 10 through the one end 92a.

In the interior of the pathway for introduction 92, a cross slit valve 94 and a valve unit 96 are installed between the site where the inflow tube 91 is perpendicularly installed and the end-plate 98. The valve unit 96 includes slitted silicone plates 96A in the inside, and in between these silicone plates 96A and the cross slit valve 94 as well as the end-plate 98, plastic pacers 96B and a gel 96C for increasing the degree of adhesiveness between the plastic pacers 96B are provided as shown in FIG. 14. In the various constituent members of the valve unit 96 (silicone plates 96A, plastic pacers 96B, and gel 96C), holes allowing insertion and extraction of a catheter are formed. By combining the cross slit valve 94 and the slitted silicone plates 96A, an effect as a check valve so as to prevent the liquid that has flowed into the pathway for introduction 92 from leaking to the outside of the port for catheter introduction 98a, can be realized, while insertion and extraction of a catheter is allowed. In addition, the slitted silicone plates 96A are composed of two sheets in the embodiment of FIG. 14 (composed of one sheet having a horizontal slit shape and one sheet having a vertical slit shape); however, the configuration is not limited to this, various combinations of the slit shapes and the number of plates can be employed.

The above-described heart models (right heart model 20, coronary artery model 30, and TAVI model 40, 80 or 100) are formed from a material having elasticity that is close to that of a real human heart, and thus, during a simulation, a feeling of touch that is close to the reality at the time of catheter operation may be obtained. Furthermore, during a simulation using the coronary artery model 30 or the TAVI model 40, 80 or 100, when a pulsatile flow is caused to flow in from the apex of the heart toward the aorta, the elastic main body of heart repeatedly undergoes expansion and contraction, and blood (liquid) can be sent out in the same manner as in the case of a real heart. Examples of a material having such elasticity include PVA (polyvinyl alcohol), polyurethane, an epoxy resin, an unsaturated polyester, a phenolic resin, silicone, or materials analogous to these, and other thermosetting resins or thermoplastic resins, which may be used singly or in combination of a plurality of materials. Thereby, training of a catheter operation can be carried out with a tactile sensation that is close to that of a human organ.

Furthermore, when the heart models (right heart model 20, coronary artery model 30, or TAVI model 40, 80 or 100) are produced from a transparent or semi-transparent material, the trainee can directly observe the movement of the catheter, guide wire, and other devices that are inserted, by visual inspection. Furthermore, the trainee can visually recognize the behavior exhibited by an infusate that is infused through a catheter. That is, heart catheterization and treatment can be simulated while correlating the manual operation and the movement of the catheter tip. In addition, even in a case in which the heart model is produced from a material that a trainee can visually recognize, if the container 10 is covered with a lid or the like so that the heart model cannot be seen, or if X-ray illumination is performed and the image is displayed on a monitor or the like, it is also possible to comprehend the behavior of the catheter through a monitor only.

It is also preferable that the various heart models (right heart model 20, coronary artery model 30, and TAVI model 40 or 80) described above are integrally produced without having artificial joints. Thereby, a blood flow that is not observed in the human body occurring due to the joints can be prevented, and at the time of catheter insertion, the field of view being blocked by the joints can be prevented. Also, the appearance of unnatural shadows under X-ray illumination does not occur.

As a method of forming a heart model using a material that satisfies the properties such as described above, for example, the optical molding method (Japanese Patent No. 5236103) invented by the present applicant can be used. When the molding method is used, a high-precision heart model for each patient can be formed in a short time period at relatively low cost, based on the imaging data of a human organ (heart CT data). Therefore, a trainee can simulate and train a catheter operation in consideration of the blood vessel structure or the diseased site intrinsic to the patent, prior to an actual surgery. Furthermore, the catheter simulator according to the present invention can be utilized for preliminary preparation before an actual catheter operation, by selecting and examining catheters or various devices that are optimal for the patient before an examination or a surgery. As a result, it is considered that the present invention contributes to the reduction of risks such as blood vessel damages associated with replacement of the catheter, cerebral embolism, and the like; enhancement of the surgical outcomes obtainable by selecting a catheter appropriate for the anatomical characteristics of the blood vessels of the patient; and the suppression of medical expenses as a result of suppressing the use of unnecessary medical devices including catheters.

In a case in which a heart model is formed according to the optical molding method described above, since a condition close to the human body can be reproduced, the surface of the heart model is not smooth and includes fine concavities and convexities similarly to the human body. In this case, even if the heart model is produced from a transparent or semi-transparent material such as described above, since visible light is diffusely reflected at the concavo-convex surface, visibility may be deteriorated. In this case, visibility can be improved by reducing diffuse reflection by, after forming the heart model, coating the surface with the same material and smoothing the concavo-convex surface.

Since the TAVI model 100 has a detachable and reattachable aortic valve 110, the aortic valve 110 and the other parts are formed separately. However, for the same reasons as in the case of the above-mentioned other heart models, it is preferable that the aortic valve and the other parts are formed by the optical molding method or a coating technique, without having artificial joints as far as possible. According to the present embodiment, the inner ring 120 and the outer ring 130 illustrated in FIG. 9 are formed from an epoxy resin, while the other parts are formed from silicone. The material for forming the inner ring 120 and the outer ring 130 is not limited to an epoxy resin, and may be any material harder than the material for forming the other parts of the heart model (silicone according to the present embodiment), such as urethane.

Next, the method of using the container for a catheter simulation 10 and the various heart models (right heart model 20, coronary artery model 30, and TAVI model 40, 80 or 100) will be explained.

Figure 2:
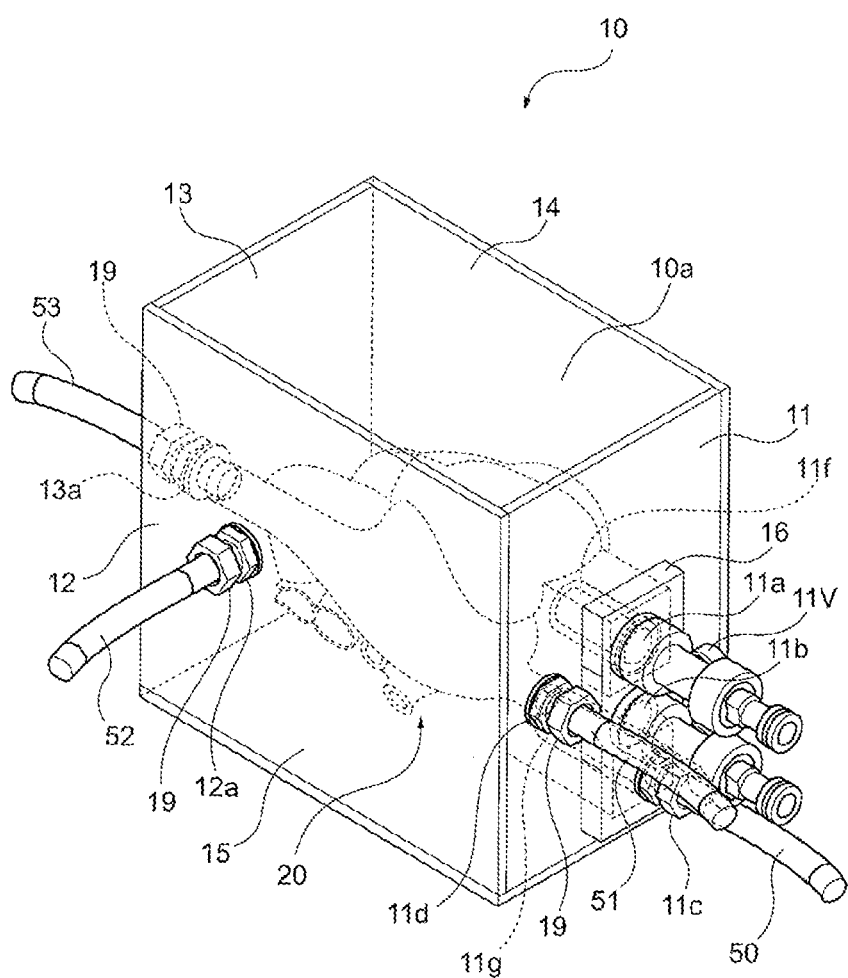
FIG. 2 is a diagram illustrating an embodiment in a case in which a right heart model, which is one of the heart models according to the present invention, is installed in the container for a catheter simulator illustrated in FIG. 1.

In the case of using the right heart model 20, as illustrated in FIG. 2, the right heart model 20 is installed in the accommodating unit 10a of the container 10 in a state in which the container 10 is filled with a liquid, as preparation.

At this time, the terminals 21a and 21b of the support unit are connected to the connection units 11a and 11c of the container, respectively, and retained in the liquid so that air does not enter the inside of the main body. The tip 22a of inferior vena cava 22 is connected to the installation part 11d of the container, and the tip 23a of the superior vena cava 23 is connected to the installation part 13a of the container.

Preparation is carried out as described above, and training of a catheter operation is initiated. In the present embodiment, two kinds of simulations, namely, a case in which a catheter is inserted through the internal jugular vein at the base of the neck, and a case in which a catheter is inserted through the femoral vein in the inguinal region, can be carried out. When the trainee simulates catheter insertion through the internal jugular vein, a catheter is introduced through the superior vena cava 23 through an inlet tube 53. The catheter introduced through the superior vena cava 23 enters the right atrium 20A1 and reaches the right ventricle 20A2. On the other hand, when the trainee simulates catheter insertion through the femoral vein, a catheter is introduced through the inferior vena cava 22 through an inlet tube 51. The catheter introduced through the inferior vena cava 22 enters the right atrium 20A1 and reaches the right ventricle 20A2.

After the catheter has reached the right atrium 20A1 and the right ventricle 20A2, simulation in accordance with the object examination or surgery are carried out; for example, catheter operations in the interior of the heart, such as mapping of measuring the electrocardiogram using an electrode mounted on the tip of the catheter and detecting the part to be treated; ablation therapy of electrically cauterizing a diseased part by means of an electrode at the catheter tip; myocardial biopsy of picking and collecting the cardiac muscles at a part that is suspected to have a disease for the purpose of a pathological examination; and right heart catheterization for measuring the pressure inside the heart or the cardiac output or the cardiac output.

Next, the case of using the coronary artery model 30 will be explained.

In this case, first, a pump 60 that produces a pulsatile flow is connected to the container 10 for catheter simulation according to the present invention. At that time, a supply tube 63 of the pump 60 is connected to the end of the connection unit 11a protruding to the outside of the container 10, such that the flow of the liquid supplied from the pump 60 enters through the connection unit 11a of the container 10. Furthermore, a discharge tube 61 of the pump 60 is connected to the discharge port 11b such that the liquid discharged from the accommodating unit 10a of the container to the pump 60 flows out to the external pump 60 through the discharge port 11b.

After the pump 60 is connected to the container 10 as such, the coronary artery model 30 is installed in the accommodating unit 10a of the container in a state in which the container 10 is filled with a liquid, as preparation. At this time, an inflow tube 31 of the coronary artery model 30 is connected to a holding protrusion 11f of the connection unit 11a of the container, an opening 32a at the end of the aorta 32 is connected to a holding protrusion 11g of the connection unit 11c of the container, and an opening 34a at the end of the right subclavian artery 34 is connected to an installation part 12a of the container, all procedures being carried out in liquid so that air does not enter the coronary artery model 30. When the system is prepared as described above, and the coronary artery model 30 is retained in a state of floating in a liquid, the coronary artery model can be made to pulsate similarly to a real heart, due to the pulsatile flow flowing into the model from the pump 60.

The pump 60 that is connected to the coronary artery model 30 is intermittently driven so as to generate a pulsatile flow in the liquid. The pump 60 has a function of receiving the liquid held in the container 10 through the discharge port 11b, sending out the liquid to the inflow tube 31 at a predetermined pressure, and thereby recirculating the liquid in the container 10. For example, the pump 60 can be configured into a circulating type pump that sends out a liquid by reciprocally driving a piston by means of a driving motor. In this case, the amount of liquid sent out by a single heartbeat (corresponding to the blood pressure) can be changed by changing the stroke of the piston that is reciprocally driven, and the period of pulsation of the heart model (corresponding to the heart rate) can be changed by changing the time for one reciprocation of the piston. Specifically, a pulsatile flow close to that of the real human body can be produced by outputting a pressure of 300 mmHg at the maximum at a rate of 20 to 200 times per minute. A similar pulsatile flow can also be produced by a variable volume type pump such as a lobed pump or a tube pump. It is preferable that the pressure at which the pump sends out the liquid is set to be 300 mmHg at the maximum since, if the pressure is higher than 300 mmHg, the heartbeat is in a state that is different from the heartbeat of a real human body. That is, the heartbeat condition can be set to a heartbeat condition appropriate for each patient (appropriate for each case of a patient) by adjusting the heartbeat in the range of 0 mmHg to 300 mmHg.

On the occasion of simulating a catheter operation for a real heart, a heart rate of 20 to 200 bpm (beats per minute) is sufficient in consideration of the heartbeat of the human body that can be assumed, and in an actual heart surgery, it is considered that the surgery is performed at a heart rate in the range of about 40 to 100 bpm in most cases. Therefore, regarding the capacity of the pump 60, any specifications that can send a pulsatile flow to the heart model at a rate of 20 to 200 times per minute may be employed, and in the case of considering the load of the pump, when a pump that can send a pulsatile flow at a rate of at least 40 to 150 times per minute to the heart model is used, simulation can be carried out effectively.

Regarding the liquid that has been sent out from the pump 60 and has flowed into the main body 30A of the coronary artery model 30 through the inflow tube 31, a portion thereof flows into the coronary arteries 33, while the remaining portion reaches the aorta 32. The liquid that has flowed into the coronary arteries 33 is discharged to the outside of the heart model 30 through a discharge port 33a provided at the end of the coronary arteries 33, and joins the liquid held in the container 10. Meanwhile, the liquid that has flowed into the aorta 32 is discharged into the container 20 through carotid arteries 35 and 36 and left subclavian artery 37, which are blood vessels provided on the pathway of the aorta 32, and joins the liquid held in the container 20. The liquid that has been discharged into the container 10 through the respective end openings of the coronary arteries 33, the carotid arteries 35 and 36, and the left subclavian artery 37, flows out through the discharge port 11b and is circulated to the pump 60. In this case, it is preferable to install a filter (not show in the diagram) that removes foreign materials at the discharge port 11b. When such a filter is installed, even if foreign materials or the like are incorporated into the container during a simulation, the foreign materials are eliminated at the discharge port area and do not affect the operation of the pump 60.

In the case of using the coronary artery model 30, training for a catheter operation is initiated in a state in which a simulated blood flow is generated as such. According to the present embodiment, two kinds of simulations, namely, the case of inserting a catheter through the artery of an arm and the case of inserting a catheter through the artery of the inguinal region, can be carried out. In a case in which a trainee simulates catheter insertion through the artery of an arm, the catheter is introduced through the right subclavian artery 34 via an inlet tube 52. The catheter introduced through the right subclavian artery 34 enters carotid artery 35, passes through the carotid artery 35, and reaches the aorta 32. Subsequently, when the catheter is further inserted, the catheter passes the interior of the aorta 32 and is positioned at an inlet port of the coronary arteries 33 (corresponding to the coronary artery inlet) that are branched in the vicinity of the connection unit of the main body 30A. At this time, the trainee locates the inlet while watching the coronary artery 33 that serves as an object of insertion (object of treatment) between the right and left coronary arteries, and performs an operation such that the catheter is engaged with the inlet part of the coronary artery to which the operation is intended. That is, the trainee can receive training equivalent to actual catheterization and surgery (coronary arteriography and coronary angioplasty), such as an operation of operating a catheter with regard to coronary arteries 33 having a thin and complicated shape to engage the catheter with the inlet part of the coronary arteries while watching the coronary artery that needs to be treated, subsequently inserting a guide wire that is needed for the treatment to the target site, and performing angioplasty by means of a balloon catheter or placement of a stent (metal cylinder) along the guide wire.

Meanwhile, in a case in which the trainee simulates catheter insertion through the artery in the inguinal region, a catheter is introduced through the caudal side end of the aorta 32 (part corresponding to the inguinal region) via an inlet tube 50. The catheter passes through the inside of the aorta 32 and reaches the inlet port of the coronary arteries 33 provided at the connection part between the aorta 32 and the main body 30A. In this case, the pathway for catheter introduction is only the pathway of the aorta 32; however, since a junction between the carotid arteries 35 and 36 and the right subclavian artery 37 exists on that pathway, at the time of operating a catheter, training of operating the catheter to reach the inlet port that corresponds to the inlet port of the coronary arteries while checking the positional relations between various simulated blood vessels, can be achieved. The trainee can receive the training for catheterization and surgery in the same manner as in the case of performing an operation with the blood vessels of the arm.

Next, the case of using the TAVI model 40 will be explained.

First, similarly to the case of using the coronary artery model 30 described above, the pump 60 is connected to the container 10 for catheter simulation. At that time, a supply tube 63 of the pump 60 is connected to an end of the connection unit 11a protruding to the outside of the container 10, such that the flow of the liquid supplied from the pump 60 enters through the connection unit 11a of the container 10. Furthermore, the discharge tube 61 is connected to the discharge port 11b such that the liquid discharged from the accommodating unit 10a of the container to the pump 60 flows out to the pump 60 through the discharge port 1ib.

After the pump 60 is connected to the container 10 as such, the TAVI model 40 is installed in the accommodating unit 10a of the container in a state in which the container 10 is filled with a liquid, as preparation. At this time, an inflow tube 41 of the TAVI model 40 is connected to a holding protrusion 11f of the connection unit 11a of the container, the end 45a of the aorta 45 is connected to a holding protrusion 11g of the connection unit 11c of the container, an opening 42a at the end of the inferior vena cava 42 is connected to an installation part 11d of the container, and an opening 43a at the end of the superior vena cava 43 is connected to the installation part 13a of the container, all procedures being carried out in liquid so that air does not enter the TAVI model 40.

When the system is prepared as described above, and the TAVI model 40 is retained in a state of floating in a liquid, the TAVI model can be made to pulsate similarly to a real heart, due to the pulsatile flow flowing into the model from the pump 60. As described above, the pump 60 is intermittently driven so as to generate a pulsatile flow in the liquid, by employing specifications similar to the case of being connected to the coronary artery model 30.

The liquid that has been sent out from the pump 60 and has flowed into the main body of the TAVI model 40 through the inflow tube 41, mainly flows into the aorta 45 through the left ventricle 40A4, and a portion thereof flows to the coronary arteries, while the remaining portion flows from the aorta to the common carotid arteries, the subclavian arteries, and the descending aorta. The diagram simply describes only the parts that constitute the skeleton of the TAVI model; however, as illustrated in FIG. 4, the TAVI model may also include coronary arteries 33, common carotid arteries 35 and 36, and subclavian arteries 34 and 37.

In the case of using the TAVI model 40, training of the catheter operation is initiated in a state in which a simulated blood flow is produced as such. In the present embodiment, simulations of the case in which a catheter is inserted through the artery and the vein in the inguinal region, the case in which a catheter is inserted through the apex of the heart, the case in which a catheter is inserted through a subclavian artery, and the case in which a catheter is inserted through the vein at the base of the neck, can be primarily carried out. In the case of introducing a catheter through the artery in the inguinal region, the catheter is inserted through the caudal side end of the aorta 45 via the inlet tube 50. Subsequently, the catheter moves toward the main body of heart along the pathway of the aorta 45 and reaches the vicinity of the connection part leading to the left ventricle 40A2. At the connection part leading to the left ventricle 40A2, an aortic valve for preventing backflow of the blood flow exists in a real human body, and as a treatment for aortic valve stenosis in which an aortic valve stiffens, and thereby the area through which blood can pass through is narrowed, a surgery of implanting an artificial valve in place of the aortic valve (TAVI or TAVR; transcatheter aortic valve implantation) is performed. In the present embodiment, since the heart model has a structure equipped with an aortic valve, on the occasion of simulating TAVI, training can be carried out by bringing an artificial valve that has been folded into a smaller size to the vicinity of the connection part between the aorta 45 and the left ventricle 40A2 by means of a catheter, and then expanding the artificial valve and fixing the artificial valve at a predetermined position by means of the catheter. Furthermore, a treatment of operating only a balloon catheter instead of a catheter mounted with an artificial valve and expanding the aortic valve by swelling the balloon at the site of the valve, that is, balloon aortic valvuloplasty (BAV), can also be implemented.

In the case of simulating the approach through the apex of the heart, a catheter is introduced to the left ventricle 40A4 through an inflow tube 41 and reaches the vicinity of the aortic valve. Furthermore, in the case of simulating the approach through a subclavian artery, a catheter is introduced to the aorta 45 through the right subclavian artery 46 and reaches the vicinity of the aortic valve. Thereafter, simulation can be carried out with a flow that is almost the same as in the case of the approach through the artery in the inguinal region.

Meanwhile, in a case in which the trainee simulates catheter insertion through the artery at the base of the neck, a catheter is introduced through the superior vena cava 43 via an inlet tube 53 and reaches the right atrium 40A1. Similarly, in the case of introducing a catheter through the vein in the inguinal region, a catheter is introduced through the inferior vena cava 42 via an inlet tube 51 and reaches the right atrium 40A1. In any of the cases, the catheter that has reached the right atrium 40A1 subsequently passes through the inside of the right atrium and enters the right ventricle 40A2 formed at the end of the right atrium 40A1. At the boundary between the right atrium 40A1 and the right ventricle 40A2, a tricuspid valve (not shown in the diagram) that prevents backflow of the blood, similarly to the human body, is provided. Furthermore, when the catheter passes through the right ventricle 40A2, the catheter reaches the pulmonary artery 44. At the boundary between the right ventricle 40A2 and the pulmonary artery 44, a pulmonary artery valve (not shown in the diagram) that prevents backflow of the blood is provided, similarly to the human body. When the trainee uses the TAVI model according to the present embodiment, the trainee can perform simulation of catheterization also for these tricuspid valve and pulmonary artery valve similarly to that for the aortic valve described above.

Next, the case of using a second embodiment 80 of the TAVI model will be explained.

First, similarly to the case of using the TAVI model 40 described above, a pump 60 is connected to a container 10 for catheter simulation, and then the TAVI model 80 is installed in the accommodating unit 10*a* of the container in a state in which the container 10 is filled with a liquid as preliminary preparation. At this time, an inflow tube 81 of the TAVI model 80 is connected to a holding protrusion 11*f* of the connection unit 11*a* of the container, and the end 82*a* of the aorta 82 is connected to a holding protrusion 11*g* of the connection unit 11*c* of the container, all procedures being carried out in a liquid so as to prevent air from entering the TAVI model 80. In the case of using the extension member 140 described above, the base 142 of the extension member is connected to the holding protrusion 11*f*, and then the TAVI model 80 is installed. In this case, the inflow tube 81 is connected to the base 142.

When the system is prepared as described above, and the TAVI model 80 is maintained in a state of floating in a liquid, the TAVI model can be made to pulsate similarly to a real heart, due to the pulsatile flow flowing into the model from the pump 60. As described above, the pump 60 is intermittently driven so as to generate a pulsatile flow in the liquid, by employing specifications similar to the cases of being connected to the coronary artery model 30 and the TAVI model 40.

The liquid that has been sent out from the pump 60 and has flowed into the main body of het TAVI model 80 through the inflow tube 81, passes through the aortic valve 82A from the main body of heart 80A and flows into the aorta 82. Regarding the liquid that has flowed into the aorta 82, a portion thereof flows into the coronary arteries 83 and is discharged to the outside of the TAVI model 80 through the discharge port 83*a* provided at the end of the coronary arteries 83, and the portion of the liquid joins the liquid held in the container 10. Meanwhile, the liquid that flows along the aorta 82 passes through the carotid arteries 85 and 86 and the subclavian arteries 84 and 87, which are blood vessels provided along the pathway of the aorta 82, and is discharged into the container 10, thereby joining the liquid held in the container 10. The liquid discharged to the container 10 through the respective end openings of the coronary arteries 83, the carotid arteries 85 and 86, and the subclavian arteries 84 and 87, flows out through the discharge port 11*b* and is circulated by the pump.

In the case of using the TAVI model 80, training of a catheter operation is initiated in a state in which a simulated blood flow is generated as such. In the present embodiment, simulation of the case in which a catheter is inserted through the artery in the inguinal region and the case in which a catheter is inserted through the apex of the heart, can be primarily carried out. The approach through the artery in the inguinal region imposes less burden to the body of the patient; however, since the pathway to reach the heart is long, this approach is not suitable as a pathway for catheter introduction in a case in which meandering of the blood vessels is complicated, or calcification is observed in the blood vessels. In that case, the approach through the apex of the heart, by which the port for catheter introduction is opened by sticking a needle into the heart, is a promising technique.

In the case of introducing a catheter through the artery in the inguinal region, the catheter is inserted through the caudal side end of the aorta 82 via the inlet tube 50. Subsequently, the catheter moves toward the main body of heart along the pathway of the aorta 82 and reaches the vicinity of the aortic valve 82A. As a treatment for aortic valve stenosis in which an aortic valve stiffens, and thereby the area through which blood can pass through is narrowed, a surgery of implanting an artificial valve in place of the aortic valve (TAVI or TAVR; transcatheter aortic valve implantation) is performed. On the occasion of simulating TAVI, training can be carried out by bringing an artificial valve that has been folded into a smaller size to the vicinity of the aortic valve 82A by means of a catheter, and then expanding the artificial valve and fixing the artificial valve at a predetermined position by means of the catheter. Furthermore, a treatment of operating only a balloon catheter instead of a catheter mounted with an artificial valve and expanding the aortic valve by swelling the balloon at the site of the valve, that is, balloon aortic valvuloplasty (BAV), can also be implemented.

In the case of simulation by visual inspection, the point marks drawn at the bottom face of three valve cusps of the aortic valve 85A described above can be used as the reference for the position for expanding an artificial valve or swelling a balloon. The point marks serve as an effective assistance means for a novice trainee. In the case of performing simulation by X-ray illumination or the like, when a radio-opaque material is used for these point marks, the point marks can also be used as markers when simulation is performed as so-called as opaque markers, even under X-ray illumination. Furthermore, by injecting a contrast agent, the positional relation between the aortic valve 85A and the catheter is understood, and the position for expanding an artificial valve or swelling a balloon is confirmed.

Meanwhile, in the case of simulating the approach through the apex of the heart, a catheter is introduced into the main body of heart 80A through an inflow tube 81 and reaches the vicinity of the aortic valve 82A. Thereafter, simulation can be carried out with a flow that is almost the same as in the case of the approach through the artery in the inguinal region. In this case, the catheter is introduced through the inflow tube 81 while maintaining the flowing in of a pulsatile flow through the inflow tube 81 by means of the two-way cock 70 described above.

Next, the case of using a third embodiment 100 of the TAVI model will be explained.

First, similarly to the case of using the TAVI model 40 or 80 described above, a pump 60 is connected to a container 10 for catheter simulation, and then the TAVI model 100 is installed in the accommodating unit 10a of the container in a state in which the container 10 is filled with a liquid as preliminary preparation.

On the occasion of installation, an inflow tube 101 of the TAVI model 100 is connected to a holding protrusion 11f of the connection unit 11a of the container, and also, the end 102a on the leg side of the aorta 102 is connected to a holding protrusion 11g of the connection unit 11c of the container, all procedures being carried out in a liquid so as to prevent air from entering the TAVI model 100. In the case of using the extension member 140 described above, the base 142 of the extension member is connected to the holding protrusion 11f, and then the TAVI model 100 is installed. In this case, the inflow tube 101 is connected to the base 142.

Here, in the TAVI model 100, the aortic valve 110 is mounted before the container is installed. However, in the case of continuously performing simulation and repeating detachment and reattachment of the aortic valve 110, the inflow tube 101 may be removed from the holding protrusion 11f (in the case of using the extension member 140, the base 142) while the TAVI model 100 is installed, only the aortic valve 110 (may also include a stent valve placed therein) may be taken out through the opening 101a of the inflow tube 101, and then only the aortic valve 110 may be inserted and mounted through the opening 101a as follows.

In that case, the aortic valve 110 enters into the interior of the main body of heart 100A through the opening 101a of the inflow tube, in a state in which the left ventricle outflow path unit 112 is retained by the user, with the valve cusp unit 110A being arranged to head forward, and is inserted into the opening 102b of the aorta. After the insertion, the annulus part 114 is connected to the periphery 102c of the opening 102b, and thereby, the aortic valve 110 is fixed and mounted at the end of the aorta 102. The fixing method is as described above.

When the system is prepared as described above, and the TAVI model 100 is retained in a state of floating in a liquid, the TAVI model can be made to pulsate similarly to a real heart, due to the pulsatile flow flowing into the model from the pump 60. As described above, the pump 60 is intermittently driven so as to generate a pulsatile flow in the liquid, by employing specifications similar to the case of being connected to the coronary artery model 30, or the TAVI model 40 or 80.

The liquid that has been sent from the pump 60 and has flowed into the main body of the TAVI model 100 through the inflow tube 101, passes through the aortic valve 110 from the main body of heart 100A and flows into the aorta 102. The aortic valve 110 can be detached and reattached; however, the aortic valve 110 is fixed so that the aortic valve is not detached by the liquid flow coming from the pump. Regarding the liquid that has flowed into the aorta 102, a portion thereof flows into the coronary arteries 103 and is discharged to the outside of the TAVI model 100 through the discharge port 103a provided at the end of the coronary arteries 103, and the portion of the liquid joins the liquid held in the container 10. Meanwhile, the liquid that flows along the aorta 102 passes through the carotid arteries 105 and 106 and the subclavian arteries 104 and 107, which are blood vessels provided on the pathway of the aorta 102, and is discharged into the container 10. Thus, the liquid joins the liquid held in the container 10. The liquid discharged into the container 10 through the respective end openings of the coronary arteries 103, the carotid arteries 105 and 106 and the subclavian arteries 104 and 107 flows out through the discharge port 11b and is circulated by the pump.

In the case of using the TAVI model 100, training of a catheter operation is initiated in a state in which a simulated blood flow has been generated as such. In the present embodiment, simulation of the case in which a catheter is inserted through the artery in the inguinal region and the case in which a catheter is inserted through the apex of the heart can be primarily carried out. The approach through the artery in the inguinal region imposes less burden to the body of the patient; however, since the pathway to reach the heart is long, the approach is not suitable as a pathway for catheter introduction in a case in which meandering of the blood vessels is complicated, or calcification is observed in the blood vessels. In that case, the approach through the apex of the heart, by which the port for catheter introduction is opened by sticking a needle into the heart, is a promising technique.

In the case of introducing a catheter through the artery in the inguinal region, the catheter is inserted through the end 102b of the aorta 102 via the inlet tube 50. Subsequently, the catheter moves toward the main body of heart along the pathway of the aorta 102 and reaches the vicinity of the aortic valve 110A. After the catheter reaches the aortic valve 110A, a surgical operation of TAVI or BAV can be simulated similarly to the simulation of the TAVI model 80. Meanwhile, in the case of simulating the approach through the apex of the heart, a catheter is introduced into the main body of heart 100A through an inflow tube 101 and reaches the vicinity of the aortic valve 110A. Thereafter, simulation can be carried out with a flow that is almost the same as in the case of the approach through the artery in the inguinal region. In this case, the catheter is introduced through the inflow tube 101 while maintaining the flowing in of a pulsatile flow through the inflow tube 101 by means of the two-way cock 70 described above.

In addition, similarly to the markers of the aortic valve 82A (point marks of the valve cusps) in the TAVI model 80, the positional relation between the aortic valve 110 and the catheter can be comprehended by taking the markers of the aortic valve 110 described above (markers at the annulus part) as the reference for the position for expanding an artificial valve or swelling a balloon, or by injecting a contrast agent. Furthermore, markers may be attached linearly in the marginal region of the valve cusps, or both the point marks of the valve cusps and the markers of the annulus part may be provided to be used in combination.

After completion of the simulation, the aortic valve 110 having a stent valve (not shown in the diagram) placed therein can be removed from the TAVI model 100, and the stent valve can be manually detached from the aortic valve. On the occasion of removing the aortic valve, engagement is released by inserting a hand through the opening 101a of the inflow tube 101, and holding and rotating the left ventricle outflow path unit 112, and then the aortic valve 110 is returned into the inflow tube 101 and is taken out to the outside of the TAVI model 100. The same operation may also be carried out using forceps, scissors, clips or the like instead of the hand.

Meanwhile, in the TAVI model 40 or 80 in which the aortic valve cannot be detached and reattached, in order to detach the stent valve, an operation of inserting forceps, scissors, clips or the like with long hafts through the inflow tube 41 or 81, causing the clips at the end to reach the vicinity of the aortic valve so as to sandwich the stent valve, returning the clip ends holding the stent valve to pass through the inside of the inflow tube, and taking out the stent valve to the outside of the TAVI model, is carried out. At this time, in stent valves made of the above-mentioned shape memory alloy or the like, since the stent valve adheres closely to the inner surface of the aortic valve so as to expand the aortic valve in the diameter direction, there are stent valves that cannot be easily detached even if the stent valve is grabbed with scissors or clips. In the TAVI model 100, since the stent valve can be manually detached by taking out the aortic valve having the stent valve placed therein, an enhancement of operability can be promoted.

As described above, when the container 10 for a catheter simulator described above is used, heart catheter procedures of a plurality of patterns in accordance with the mode of examination or surgery can be continuously trained more conveniently. Furthermore, depending on the kind, details, procedure and the like of simulation, a trainee can receive training for catheter operations for various types of heart diseases by switching the heart model to be connected to the container, while using the same container, without needing to replace the liquid held in the container. Furthermore, in the present embodiment, the connection and use of the external pulsatile flow-producing pump can be selected depending on the heart model to be connected to the container. Thus, the present embodiment is configured such that various heart models can be switched, and the use of an external pump can also be selected. Thereby, in regard to a catheter treatment that greatly affects the heartbeat, simulation can be carried out at a heartbeat that is close to the reality, by causing a pulsatile flow to flow into the heart model.

In the container 10, since a heart model can be retained in a state of floating the heart model at the connection units 11a and 11c provided on the side walls of the container 10, the container 10 does not need another holder for exclusive use or the like, and miniaturization and weight reduction can be achieved. Thereby, the range of selection for the place of performing simulation becomes wider, and also, a trainee can carry out setting up or cleaning up of simulations by himself or herself, without the restriction on employing assistants.

When the heart model (coronary artery model 30, right heart model 20, or TAVI model 40, 80 or 100) that is accommodated in such a container is used, not only catheter procedures such as a treatment for the coronary arteries at the heart surface, coronary arteriography, and coronary angioplasty, but also catheter operations such as mapping for diseases concerning the interior of the heart, ablation therapy, and tissue collection for myocardiac biopsy, or transcatheter aortic valve implantation can be continuously simulated. In regard to a treatment for the coronary arteries that greatly affects the heartbeats, and transcatheter aortic valve implantation, simulation can be carried out at a heartbeat that is close to the reality, due to the pulsatile flow that flows into the heart model, by using an external pump.

Furthermore, since the various heart models described above can be produced based on CT images of actual patients or based on individual cases, preoperative simulation can be carried out for each case. In the present invention, since the heart model can be simply switched, an environment for training can be provided as a general-purpose model for practice to novice trainees such as medical students or medical interns, and the present invention can also be used by experts for the training of cases with high difficulties. That is, a heart model can be molded based on heart CT data that have been captured in advance, and simulation can be carried out before an actual surgery.

Thus, exemplary embodiments of the container for a catheter simulator according to the present invention and the various heart models accommodated in the container have been described; however, the present invention is not intended to be limited to the embodiments described above, and various modifications can be applied to the extent that the gist of the present invention is maintained. For example, the shape of the container or the two-way cock, the position of installation of the connection unit and the installation part, and the like can be modified as appropriate.

EXPLANATIONS OF LETTERS OR NUMERALS

10 Container for catheter simulator
11a, 11c Connection unit
11b Discharge port
11d, 12a, 13a Catheter installation part
15 Bottom face
16 Auxiliary plate
20 Right heart model
20A1 Right atrium
20A2 Right ventricle
20A4 Left ventricle
21 Support unit
30 Coronary artery model
31 Inflow tube
33 Coronary artery
40 TAVI model
40A1 Right atrium
40A2 Right ventricle
40A4 Left ventricle
41 Inflow tube
60 Pulsatile flow-producing pump
70 Two-way cock
71 Inflow tube
80 TAVI model
80A Main body of heart
81 Inflow tube
82 Aorta
82A Aortic valve
82A1, 82A2, 82A3 Valve cusp
100 TAVI model
100A Main body of heart
101 Inflow tube
102 Aorta
102b Opening of aorta
102c Opening periphery of aorta
102B Protrusion of opening periphery of aorta
102E Convexity of protrusion of opening periphery of aorta
110 Aortic valve
110A Valve cusp unit
112 Left ventricle outflow path part
114 Annulus part
114B Protrusion of annulus part
114E Concavity of protrusion of annulus part
116 Placing part 120 Inner ring
130 Outer ring
200 Fixing base

What is claimed is:

1. A heart model retained in a container for a catheter simulator comprising:
the heart model having a simulated blood vessel, and
the container for the catheter simulator including:
an accommodating unit for accommodating a liquid, the accommodating unit having side walls and a bottom surface,
a connection unit attached to one of the side walls and retaining the heart model, and
an installation part provided on one of the side walls, the installation part being configured to insert a catheter from an outside of the container into the simulated blood vessel of the heart model,
wherein the connection unit is provided on the side wall and includes a holding protrusion protruding inside the accommodating unit,
the connection unit having the holding protrusion includes a communicating hole,
a front end of the holding protrusion protruding into the accommodating unit is open so that the heart model is detachable from and reattachable to the holding protrusion by inserting and extracting a terminal of the heart model, and
the holding protrusion retains the heart model in a state of floating in the liquid retained in the accommodating unit such that neither holding protrusion nor the heart model are in physical contact with the bottom surface.

2. The heart model according to claim 1, wherein the heart model is a four-chamber heart model formed from an elastic material, consisting of right atrium, right ventricle, left atrium and left ventricle, and having a support unit connectable to the connection unit.

3. The heart model according to claim 1, wherein the heart model is formed from an elastic material so as to have coronary arteries on a surface, and an inflow tube capable of being connected to the connection unit.

4. The heart model according to claim 1, wherein the heart model is a Transcatheter Aortic Valve Implantation model comprising a main body formed from an elastic material, an aorta protruding into an interior of the main body of a heart, an aortic valve positioned at an end of the aorta, and an inflow tube capable of being connected to the connection unit.

5. The heart model according to claim 4, wherein the aortic valve has valve cusps, and the valve cusps have markers.

6. The heart model according to claim 5, wherein the aortic valve positioned at the end of the aorta is detachable and reattachable.

7. The heart model according to claim 6, wherein the detachable and reattachable aortic valve includes valve cusps, a cyclic annulus part at a bottom of the valve cusps, and a left ventricle outflow path unit connected to the annulus part and serving as a handle at a time of detachment and reattachment.

8. The heart model according to claim 7, wherein
the annulus part of the aortic valve includes an inner ring on an outer side,
the aorta includes an outer ring on an inner side of an opening periphery of the aorta, the outer ring being connected to the inner ring,
the inner ring includes a protrusion having a concavity, and
the outer ring includes a protrusion having a convexity for being connected to the concavity.

9. The heart model according to claim 8, wherein the inner ring or the outer ring has a marker for position adjustment of the aortic valve to a predetermined position of the aorta.

10. The heart model according to claim 4, wherein the aortic valve includes a placing part in an inside.

11. The heart model according to claim 2, wherein the heart model has a surface coated with a same material as the material used for forming the heart model.

12. The heart model according to claim 3, wherein the heart model has a surface coated with a same material as the material used for forming the heart model.

13. The heart model according to claim 2, wherein the heart model is integrally formed without having any artificial joints.

14. The heart model according to claim 3, wherein the heart model is integrally formed without having any artificial joints.

15. The heart model according to claim 6, wherein parts other than the aortic valve in the heart model are integrally formed without having any artificial joints.

* * * * *